(12) United States Patent
Liu et al.

(10) Patent No.: US 12,558,168 B2
(45) Date of Patent: Feb. 24, 2026

(54) SPATIAL POSITIONING METHOD, RELATED APPARATUS, AND NAVIGATION STICK

(71) Applicant: Tencent Technology (Shenzhen) Company Limited, Shenzhen (CN)

(72) Inventors: Yixun Liu, Shenzhen (CN); Chenchen Qin, Shenzhen (CN); Jianhua Yao, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 954 days.

(21) Appl. No.: 17/746,775

(22) Filed: May 17, 2022

(65) Prior Publication Data

US 2022/0273376 A1     Sep. 1, 2022

Related U.S. Application Data

(63) Continuation of application No. PCT/CN2021/098817, filed on Jun. 8, 2021.

(30) Foreign Application Priority Data

Jul. 21, 2020   (CN) .......................... 202010707497.6

(51) Int. Cl.
*A61B 34/20*           (2016.01)
(52) U.S. Cl.
CPC ...... *A61B 34/20* (2016.02); *A61B 2034/2055* (2016.02); *A61B 2034/2068* (2016.02)
(58) Field of Classification Search
CPC ............ A61B 34/20; A61B 2034/2055; A61B 2034/2068; A61B 2034/2065; A61B 2090/3983
See application file for complete search history.

(56) References Cited

U.S. PATENT DOCUMENTS 5,868,675 A      2/1999   Henrion et al.
2009/0325135 A1   12/2009   Huang et al.
(Continued)

FOREIGN PATENT DOCUMENTS

CN        101697869 A      4/2010
CN        101862220 A     10/2010
(Continued)

OTHER PUBLICATIONS

Tencent Technology (Shenzhen) Company Limited, Japanese Office Action, JP 2022-550861, Oct. 3, 2023, 12 pgs.
(Continued)

*Primary Examiner* — Benjamin O Dulaney
(74) *Attorney, Agent, or Firm* — Morgan, Lewis & Bockius LLP

(57) ABSTRACT

This application discloses a spatial positioning method and related apparatus, and a navigation stick. The method includes: determining three-dimensional position coordinates of marker points on an outer surface of the navigation stick included in an image from a camera in a three-dimensional coordinate system corresponding to the navigation stick according to marker point information; determining position information of the camera in the three-dimensional coordinate system corresponding to the navigation stick; determining a spatial transformation relationship between the three-dimensional coordinate system corresponding to the navigation stick and a three-dimensional coordinate system corresponding to the camera; and determining, based on three-dimensional position coordinates of a to-be-detected position of the navigation stick in the three-dimensional coordinate system corresponding to the navigation stick and the spatial transformation relationship, spatial position information of the to-be-detected position of the navigation stick for spatial positioning.

19 Claims, 9 Drawing Sheets

(56)                    References Cited

U.S. PATENT DOCUMENTS

| | | | | |
|---|---|---|---|---|
| 2010/0168562 | A1* | 7/2010 | Zhao | A61B 34/30 |
| | | | | 600/426 |
| 2017/0221226 | A1* | 8/2017 | Shen | G06T 7/80 |
| 2017/0249745 | A1* | 8/2017 | Fiala | G06T 7/13 |
| 2018/0071032 | A1* | 3/2018 | de Almeida Barreto | |
| | | | | G06T 19/006 |
| 2018/0198972 | A1* | 7/2018 | Jiang | H04N 13/275 |
| 2019/0015162 | A1 | 1/2019 | Abhari et al. | |
| 2022/0333914 | A1* | 10/2022 | Belda Pla | G01B 5/0025 |

FOREIGN PATENT DOCUMENTS

| | | |
|---|---|---|
| CN | 105658167 A | 6/2016 |
| CN | 105852970 A | 8/2016 |
| CN | 107004240 A | 8/2017 |
| CN | 107874832 A | 4/2018 |
| CN | 207898557 U | 9/2018 |
| CN | 108765494 A | 11/2018 |
| CN | 110547872 A | 12/2019 |
| CN | 111821025 A | 10/2020 |
| JP | 2001204739 A | 7/2001 |
| JP | 2001293007 A | 10/2001 |
| JP | 2014170374 A | 9/2014 |
| WO | WO 2015118157 A1 | 8/2015 |

OTHER PUBLICATIONS

Tencent Technology, WO, PCT/CN2021/098817, Aug. 26, 2021, 6 pgs.
Tencent Technology, IPRP, PCT/CN2021/098817, Jan. 24, 2023, 7 pgs.
Tencent Technology, Extended European Search Report, EP Patent Application No. 21846816.3, Jan. 9, 2024, 11 pgs.
Tencent Technology, ISR, PCT/CN2021/098817, Aug. 26, 2021, 3 pgs.

* cited by examiner

Nine positions

Eight marker points

Six marker point columns

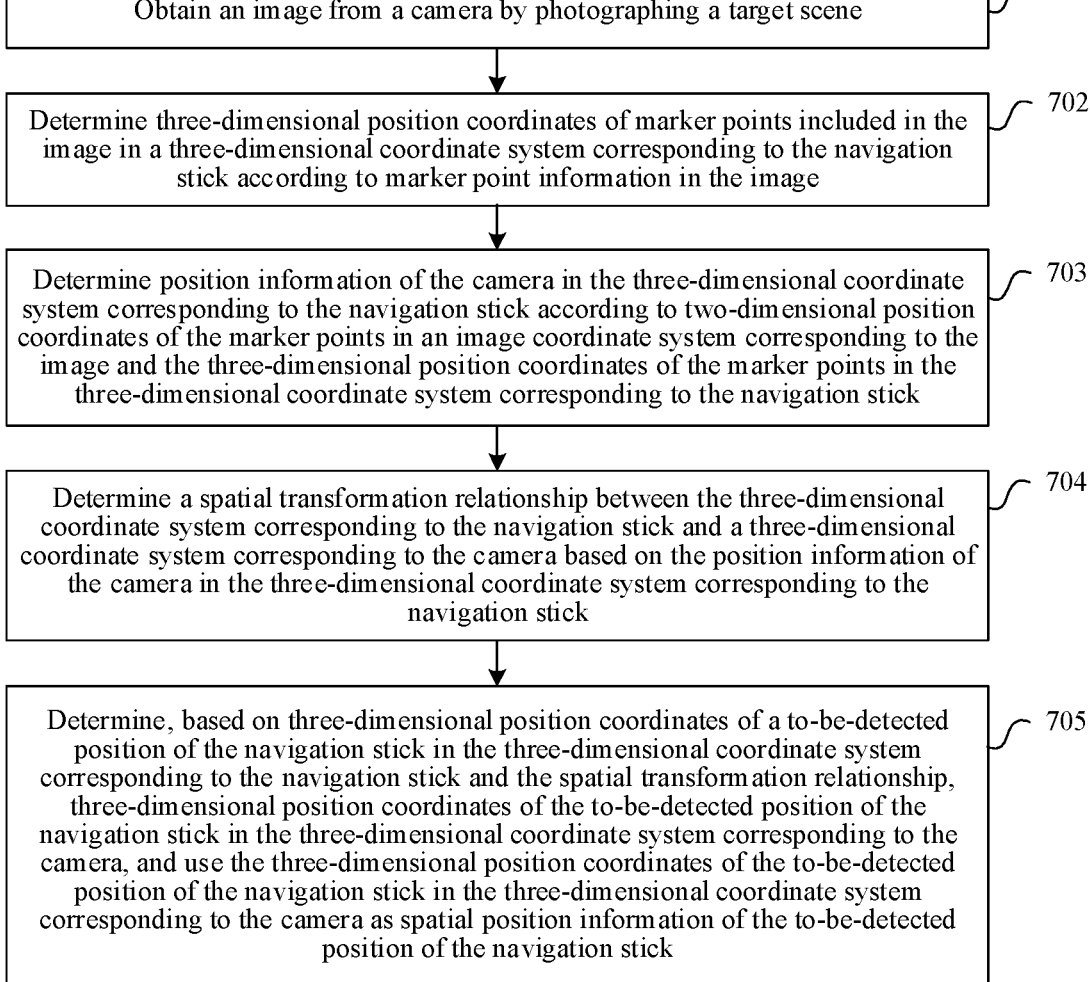

701  Obtain an image from a camera by photographing a target scene

702  Determine three-dimensional position coordinates of marker points included in the image in a three-dimensional coordinate system corresponding to the navigation stick according to marker point information in the image 703  Determine position information of the camera in the three-dimensional coordinate system corresponding to the navigation stick according to two-dimensional position coordinates of the marker points in an image coordinate system corresponding to the image and the three-dimensional position coordinates of the marker points in the three-dimensional coordinate system corresponding to the navigation stick 704  Determine a spatial transformation relationship between the three-dimensional coordinate system corresponding to the navigation stick and a three-dimensional coordinate system corresponding to the camera based on the position information of the camera in the three-dimensional coordinate system corresponding to the navigation stick 705  Determine, based on three-dimensional position coordinates of a to-be-detected position of the navigation stick in the three-dimensional coordinate system corresponding to the navigation stick and the spatial transformation relationship, three-dimensional position coordinates of the to-be-detected position of the navigation stick in the three-dimensional coordinate system corresponding to the camera, and use the three-dimensional position coordinates of the to-be-detected position of the navigation stick in the three-dimensional coordinate system corresponding to the camera as spatial position information of the to-be-detected position of the navigation stick

FIG. 7

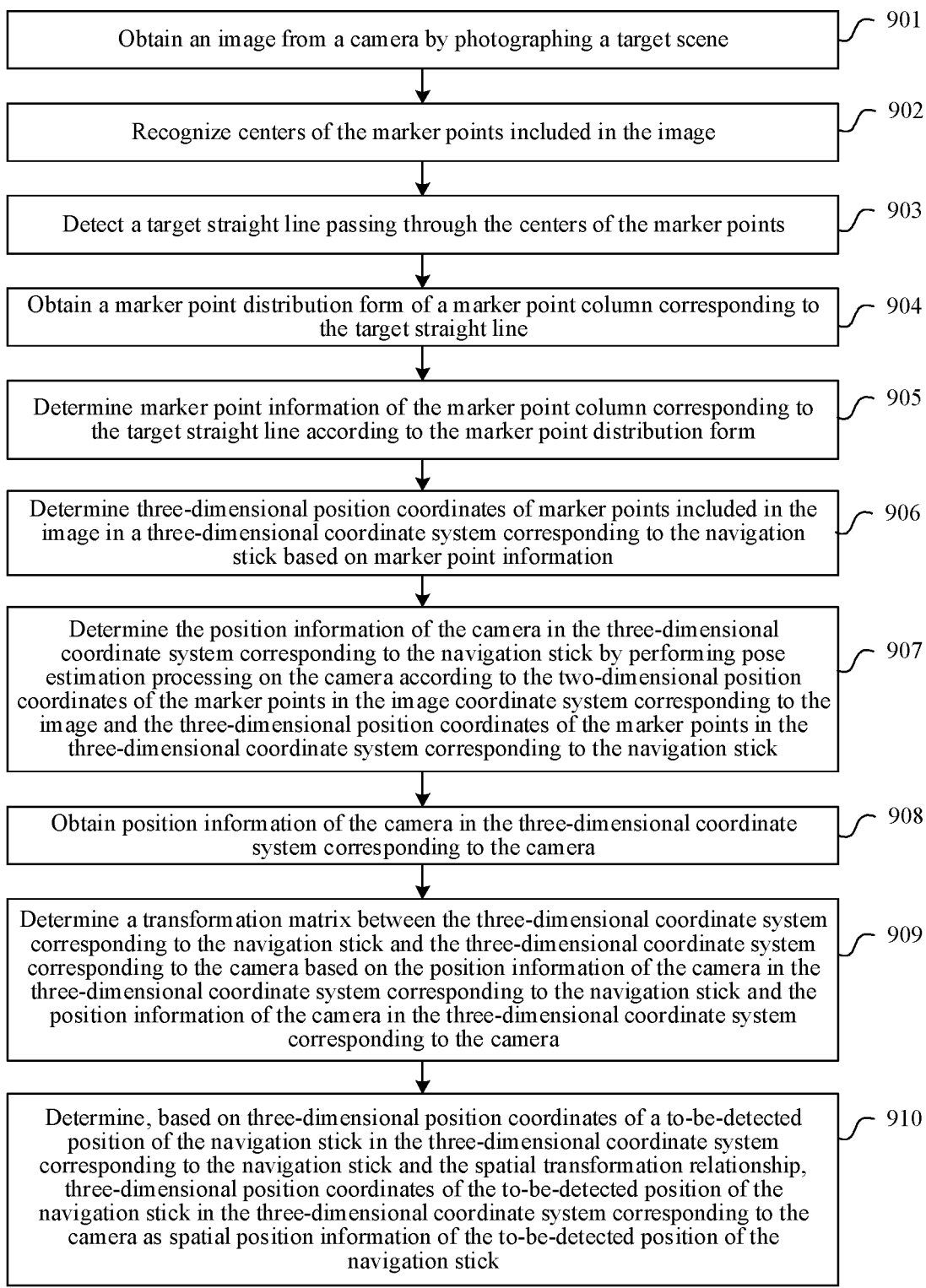

Obtain an image from a camera by photographing a target scene ⟋ 901

Recognize centers of the marker points included in the image ⟋ 902

Detect a target straight line passing through the centers of the marker points ⟋ 903

Obtain a marker point distribution form of a marker point column corresponding to the target straight line ⟋ 904

Determine marker point information of the marker point column corresponding to the target straight line according to the marker point distribution form ⟋ 905

Determine three-dimensional position coordinates of marker points included in the image in a three-dimensional coordinate system corresponding to the navigation stick based on marker point information ⟋ 906

Determine the position information of the camera in the three-dimensional coordinate system corresponding to the navigation stick by performing pose estimation processing on the camera according to the two-dimensional position coordinates of the marker points in the image coordinate system corresponding to the image and the three-dimensional position coordinates of the marker points in the three-dimensional coordinate system corresponding to the navigation stick ⟋ 907

Obtain position information of the camera in the three-dimensional coordinate system corresponding to the camera ⟋ 908

Determine a transformation matrix between the three-dimensional coordinate system corresponding to the navigation stick and the three-dimensional coordinate system corresponding to the camera based on the position information of the camera in the three-dimensional coordinate system corresponding to the navigation stick and the position information of the camera in the three-dimensional coordinate system corresponding to the camera ⟋ 909

Determine, based on three-dimensional position coordinates of a to-be-detected position of the navigation stick in the three-dimensional coordinate system corresponding to the navigation stick and the spatial transformation relationship, three-dimensional position coordinates of the to-be-detected position of the navigation stick in the three-dimensional coordinate system corresponding to the camera as spatial position information of the to-be-detected position of the navigation stick ⟋ 910

FIG. 9

SPATIAL POSITIONING METHOD, RELATED APPARATUS, AND NAVIGATION STICK

CROSS-REFERENCE TO RELATED APPLICATIONS

This application is a continuation application of PCT Patent Application No. PCT/CN2021/098817, entitled "SPATIAL POSITIONING METHOD, RELATED APPARATUS AND NAVIGATION STICK" filed on Jun. 8, 2021, which claims priority to Chinese Patent Application No. 202010707497.6, filed with the China National Intellectual Property Administration on Jul. 21, 2020, and entitled "SPATIAL POSITIONING METHOD AND APPARATUS, DEVICE, STORAGE MEDIUM, AND NAVIGATION STICK", all of which are incorporated herein by reference in their entirety.

FIELD OF THE TECHNOLOGY

This application relates to the field of artificial intelligence technologies, and in particular, to spatial positioning.

BACKGROUND OF THE DISCLOSURE

A surgical navigation system accurately corresponds preoperative or intraoperative image data of a patient with an anatomical structure of the patient on an operating bed. In the surgical navigation system, a target position needs to be spatially positioned to make the surgical operation faster, more accurate, and safer.

The conventional spatial positioning method requires the help of a host, a tracker, and a tracking tool. The tracker is connected to the host, and the tracker includes an infrared emitting apparatus and a stereo camera. The infrared emitting apparatus emits infrared rays, which are reflected by a reflection ball fixed on the tracking tool and then imaged in the stereo camera. A needle tip on the tracking tool is then positioned by using a position of the reflection ball on the tracking tool as a reference. The tracking tool is also referred to as a navigation stick clinically, which needs to move towards the tracker within a tracking range of the tracker to complete the spatial positioning.

SUMMARY

In view of this, embodiments of this application provide a spatial positioning method and related apparatus, and a navigation stick, which can expand a spatial positioning range, improve the movement flexibility of the navigation stick, and reduce the costs of spatial positioning.

To achieve the foregoing objective, the embodiments of this application provide the following technical solutions:

According to an aspect, an embodiment of this application provides a spatial positioning method, including:

obtaining an image from a camera by photographing a target scene, the image including a navigation stick located in the target scene, and an outer surface of the navigation stick having a marker point array for locating the navigation stick;

determining three-dimensional position coordinates of marker points included in the image in a three-dimensional coordinate system corresponding to the navigation stick according to marker point information in the image, the marker point information being used for indicating positions of the marker points included in the image in the marker point array; determining position information of the camera in the three-dimensional coordinate system corresponding to the navigation stick according to two-dimensional position coordinates of the marker points in an image coordinate system corresponding to the image and the three-dimensional position coordinates of the marker points in the three-dimensional coordinate system corresponding to the navigation stick;

determining a spatial transformation relationship between the three-dimensional coordinate system corresponding to the navigation stick and a three-dimensional coordinate system corresponding to the camera based on the position information of the camera in the three-dimensional coordinate system corresponding to the navigation stick; and determining, based on three-dimensional position coordinates of a to-be-detected position of the navigation stick in the three-dimensional coordinate system corresponding to the navigation stick and the spatial transformation relationship, three-dimensional position coordinates of the to-be-detected position of the navigation stick in the three-dimensional coordinate system corresponding to the camera, and using the three-dimensional position coordinates of the to-be-detected position of the navigation stick in the three-dimensional coordinate system corresponding to the camera as spatial position information of the to-be-detected position of the navigation stick.

According to another aspect, an embodiment of this application provides a spatial positioning apparatus, including:

an image obtaining module, configured to obtain an image from a camera by photographing a target scene, the image including a navigation stick located in the target scene, and an outer surface of the navigation stick having a marker point array for locating the navigation stick;

a marker determining module, configured to determine three-dimensional position coordinates of marker points included in the image in a three-dimensional coordinate system corresponding to the navigation stick according to marker point information in the image, the marker point information being used for indicating positions of the marker points included in the image in the marker point array;

a camera positioning module, configured to determine position information of the camera in the three-dimensional coordinate system corresponding to the navigation stick according to two-dimensional position coordinates of the marker points in an image coordinate system corresponding to the image and the three-dimensional position coordinates of the marker points in the three-dimensional coordinate system corresponding to the navigation stick;

a spatial transformation module, configured to determine a spatial transformation relationship between the three-dimensional coordinate system corresponding to the navigation stick and a three-dimensional coordinate system corresponding to the camera based on the position information of the camera in the three-dimensional coordinate system corresponding to the navigation stick; and a fixed point positioning module, configured to determine, based on three-dimensional position coordinates of a to-be-detected position of the navigation stick in the three-dimensional coordinate system corresponding to the navigation stick and the spatial transformation relationship, three-dimensional position coordinates of the to-be-detected position of the navigation stick in the three-dimensional coordinate system corresponding to the camera, and use the three-dimensional position coordinates of the to-be-detected position of the navigation stick in the three-dimensional coordinate system corresponding to the camera as spatial position information of the to-be-detected position of the navigation stick.

According to another aspect, an embodiment of this application provides a computer device, including a processor and a memory, the memory storing at least one instruction, at least one program, a code set, or an instruction set, and the at least one instruction, the at least one program, the code set, or the instruction set being loaded and executed by the processor to implement the foregoing spatial positioning method.

According to another aspect, an embodiment of this application provides a computer-readable storage medium, storing at least one instruction, at least one program, a code set, or an instruction set, the at least one instruction, the at least one program, the code set, or the instruction set being loaded and executed by a processor to implement the foregoing spatial positioning method.

According to another aspect, an embodiment of this application provides a computer program product including instructions, the computer program product, when run on a computer, causing the computer to perform the spatial positioning method according to the foregoing aspect.

According to still another aspect, an embodiment of this application provides a navigation stick for spatial positioning, including a stick body, a probe head, and a housing.

The probe head is connected to an end of the stick body and is configured to indicate a to-be-detected position for spatial positioning, and spatial position information of any point in space is determined by using the spatial positioning method according to the foregoing aspect.

A photographing range of a camera is used as a spatial positioning range, and only a navigation stick and a terminal are used to form a spatial positioning system. A marker point distribution pattern and marker point information of marker points in an image photographed by the camera at any angle may be extracted. Three-dimensional position coordinates of the marker points included in the image in a three-dimensional coordinate system corresponding to the navigation stick are determined through the marker point information. Two-dimensional position coordinates of the marker points in an image coordinate system corresponding to the image and the three-dimensional position coordinates determined above are used as the basis to estimate a camera pose, to obtain a spatial transformation relationship between the three-dimensional coordinate system corresponding to the navigation stick and the image coordinate system corresponding to the image. A to-be-detected position where the navigation stick is located is spatially positioned according to the spatial transformation relationship, to obtain three-dimensional position coordinates of the to-be-detected position in the three-dimensional coordinate system corresponding to the camera. Therefore, the spatial transformation relationship between the three-dimensional coordinate system corresponding to the navigation stick and the three-dimensional coordinate system corresponding to the camera is determined, so that both the camera and the navigation stick can be moved arbitrarily, which improves the movement flexibility of the navigation stick, expands the spatial positioning range, improves the flexibility of spatial positioning, and reduces the costs of spatial positioning.

BRIEF DESCRIPTION OF THE DRAWINGS

To describe the technical solutions in the embodiments of this application or in the related art more clearly, the following briefly describes the accompanying drawings required for describing the embodiments or the related art. Apparently, the accompanying drawings in the following descriptions show merely the embodiments of this application, and a person of ordinary skill in the art may still derive other drawings from the accompanying drawings without creative efforts.

FIG. 7 is a flowchart of a spatial positioning method according to an embodiment of this application.

FIG. 9 is a flowchart of a spatial positioning method according to another embodiment of this application.

DESCRIPTION OF EMBODIMENTS

Figure 1:
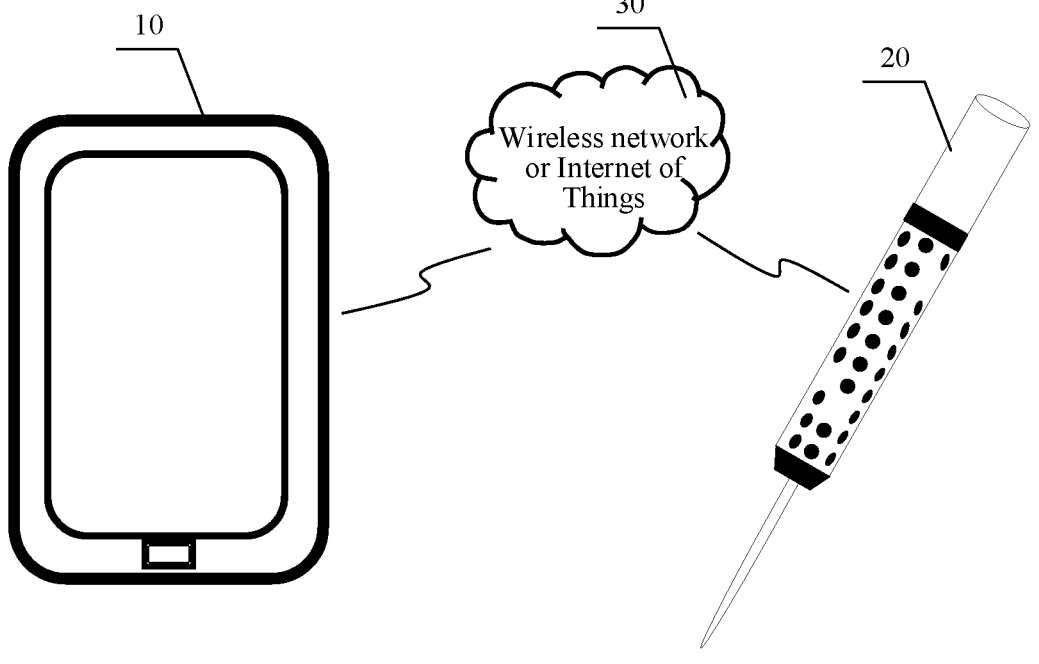
FIG. 1 is a schematic diagram of a spatial positioning system according to an embodiment of this application.

The technical solutions in the embodiments of this application are clearly and completely described below with reference to the accompanying drawings in the embodiments of this application. Apparently, the described embodiments are merely some rather than all of the embodiments of this application. All other embodiments obtained by a person of ordinary skill in the art based on the embodiments of this application without creative efforts shall fall within the protection scope of this application.

Artificial Intelligence (AI) is a theory, a method, a technology, and an application system that use a digital computer or a machine controlled by the digital computer to simulate, extend, and expand human intelligence, perceive an environment, obtain knowledge, and use knowledge to obtain an optimal result. In other words, AI is a comprehensive technology of computer science, which attempts to understand the essence of intelligence and produce a new type of intelligent machine that can react in a similar way to human intelligence. AI is to study design principles and implementation methods of various intelligent machines, so that the machines have the functions of perception, reasoning, and decision-making.

The AI technology is a comprehensive discipline, covering a wide range of fields including both hardware-level technologies and software-level technologies. The basic AI technology generally includes technologies such as sensors, dedicated AI chips, cloud computing, distributed storage, big data processing technologies, operating/interaction systems, and mechatronics. AI software technologies mainly include a computer vision technology, a speech processing technology, a natural language processing technology, machine learning/deep learning (DL), and the like.

Computer vision (CV) is a science that studies how to enable a machine to "see", and to be specific, to implement machine vision such as recognition, tracking, measurement, and the like for a target by using a camera and a computer in replacement of human eyes, and further perform graphic processing, so that the computer processes the target into an image more suitable for human eyes to observe, or more suitable to be transmitted to an instrument for detection. As a scientific subject, CV studies related theories and technologies, and attempts to establish an AI system that can obtain information from images or multidimensional data. The CV technology generally includes technologies such as image processing, image recognition, image semantic understanding, image retrieval, optical character recognition (OCR), video processing, video semantic understanding, video content/behavior recognition, three-dimensional object reconstruction, a 3D technology, virtual reality (VR), augmented reality (AR), synchronous positioning, and map construction, and further include biological feature recognition technologies such as common face recognition and fingerprint recognition.

The solutions provided in the embodiments of this application relate to the CV technologies of AI. To make objectives, technical solutions, and advantages of this application clearer, the following further describes implementations of this application in detail with reference to the accompanying drawings.

FIG. 1 is a schematic diagram of a spatial positioning system according to an embodiment of this application. The spatial positioning system may include: a terminal 10 and a navigation stick 20.

The terminal 10 may be an electronic device such as a mobile phone, a tablet computer, a game console, a wearable device, or a personal computer (PC). In some embodiments, the terminal 10 is a mobile terminal device such as a tablet computer based on an Android system. The mobile terminal device may be used to replace a PC and a tracker required in the conventional spatial positioning system, reducing a quantity of devices in the spatial positioning system. In some embodiments, there is no physical connection between the mobile terminal device and the navigation stick 20 to replace the wired connection between the conventional PC and tracker. For example, as shown in FIG. 1, the mobile terminal device and the navigation stick 20 are connected through a wireless network or an Internet of Things 30, and the mobile terminal device can spatially position the navigation stick without a tracker.

In some embodiments, a client of an application is installed in the terminal 10. In the embodiments of this application, the application may be any application that can display an image obtained by photographing a target scene, so that a user can spatially position a to-be-detected position (for example, a needle tip position) of the navigation stick in the target scene. Typically, the application is a neurosurgery navigation application. The neurosurgery navigation application is installed in the terminal 10. To complete a neurosurgery navigation function, a navigation stick needs to be equipped. The navigation stick is a surgical instrument used for spatial positioning in a neurosurgery scene. Certainly, in addition to the neurosurgery navigation application, other types of applications may also display the target scene to the user and achieve the function of spatial positioning. For example, the foregoing application may be a virtual reality (VR) application, an augmented reality (AR) application, a three-dimensional map application, a military simulation application, a graphic drawing application, a model drawing application, or the like, and this is not limited in the embodiments of this application.

Besides, the target scene and the corresponding function vary with different applications, and may be preset according to an actual requirement. This is not limited in the embodiments of this application.

The navigation stick 20 is a surgical instrument for spatial positioning. In some embodiments, an outer surface of the navigation stick has a marker point array for locating the navigation stick. The marker point array is an array formed by marker points according to a specific feature distribution, and a corresponding marker point distribution pattern may be presented in an image photographed by the camera in the terminal 10, and may be recognized by the terminal 10. Spatial position information of the navigation stick 20 can be obtained through the marker point distribution pattern in the marker point array.

In some embodiments, the neurosurgery navigation application includes three functions, namely, a spatial positioning function, a spatial ranging function, and a spatial contour line drawing function.

Figure 2:
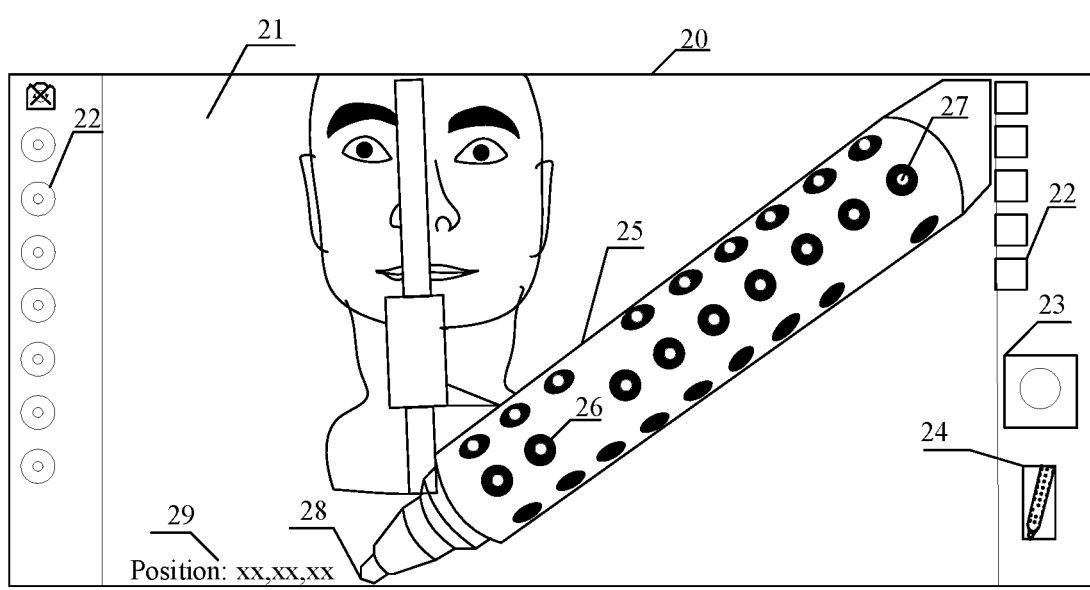
FIG. 2 is an exemplary schematic diagram of a user interface of spatial positioning.

In an example, FIG. 2 is a schematic diagram of a user interface of spatial positioning. The user interface 20 includes a target scene 21, an option button 22, a start button 23, and a function switching button 24. The target scene 21 includes a navigation stick 25, marker points 26 are distributed on an outer surface of the navigation stick 25, and a detection mark 27 is displayed at a center of the marker point. A stick tip 28 of the navigation stick is a to-be-detected position for spatial positioning, and coordinate information 29 of the stick tip 28 of the navigation stick is displayed next to the position where the stick tip 28 of the navigation stick is located. The function switching button 24 is configured to switch the spatial positioning function, the spatial ranging function, and spatial contour line drawing function. In some embodiments, each time the switching button 24 is clicked, the neurosurgery navigation application switches a function. For example, the corresponding function after the function switching button 24 is clicked for the first time is the spatial positioning function, the corresponding function after the function switching button 24 is clicked again is the spatial ranging function, the corresponding function after the function switching button 24 is clicked again is the spatial contour line drawing function, and so on.

Figure 3:
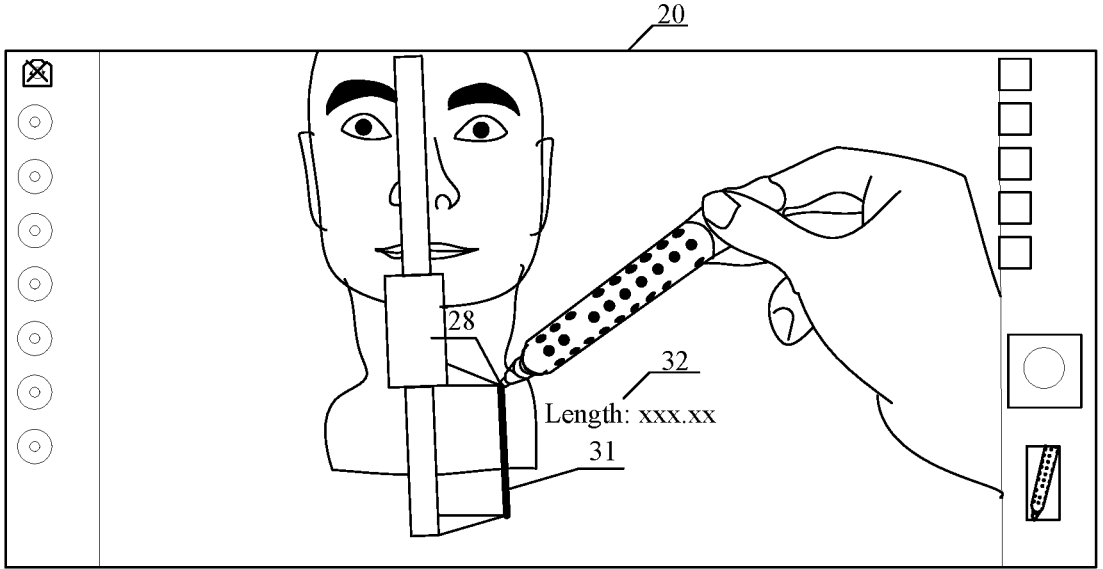
FIG. 3 is an exemplary schematic diagram of a user interface of spatial ranging.

In an example, FIG. 3 is a schematic diagram of a user interface of spatial ranging. The user interface 20 displays a connection line 31 between two positions of the stick tip 28 of the navigation stick and movement distance information 32 corresponding to the connection line 31.

Figure 4:
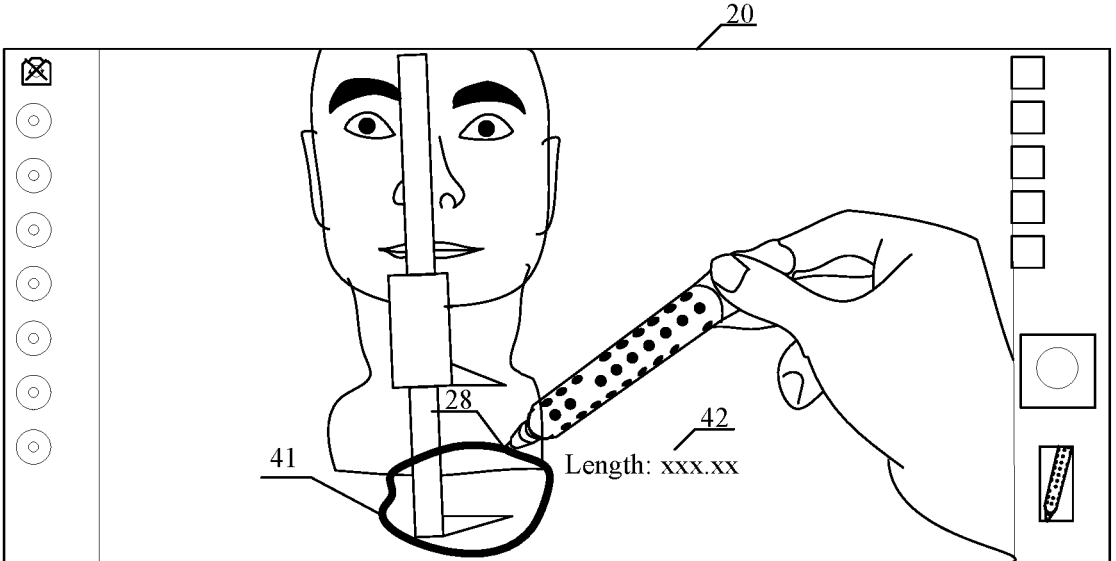
FIG. 4 is an exemplary schematic diagram of a user interface of spatial contour line drawing.

In an example, FIG. 4 is a schematic diagram of a user interface of spatial contour line drawing. A trajectory 41 formed by the stick tip 28 of the navigation stick is displayed in the user interface 20. In some embodiments, length information 42 of the trajectory 41 is displayed in the user interface 20.

In FIG. 2 to FIG. 4, only a marker pen is used instead of the navigation stick, and a pen tip position of the marker pen replaces the stick tip position of the navigation stick for illustration. The specific shape and style of the navigation stick is not limited in this application.

In an exemplary embodiment, the navigation stick 25 shown in FIG. 2 and the terminal 10 shown in FIG. 1 may constitute a neurosurgery navigation system. In some embodiments, the function switching button 24 is disposed on the navigation stick 25. In some embodiments, the terminal 10 and the navigation stick 25 are connected through short-range wireless communication to implement communication. For example, when the user presses the function switching button 24, the navigation stick 25 sends a function switching signal to the terminal 10, and the terminal 10 responds to the function switching signal and executes a program corresponding to the switched function to execute the function selected by the user. The foregoing three functions are switched by operating the function switching button 24 disposed on the navigation stick 25, which further improves the usability of the neurosurgery navigation system. The Internet of Things connection technology used between the terminal 10 and the navigation stick 25 is not limited in the embodiments of this application.

Figure 5:
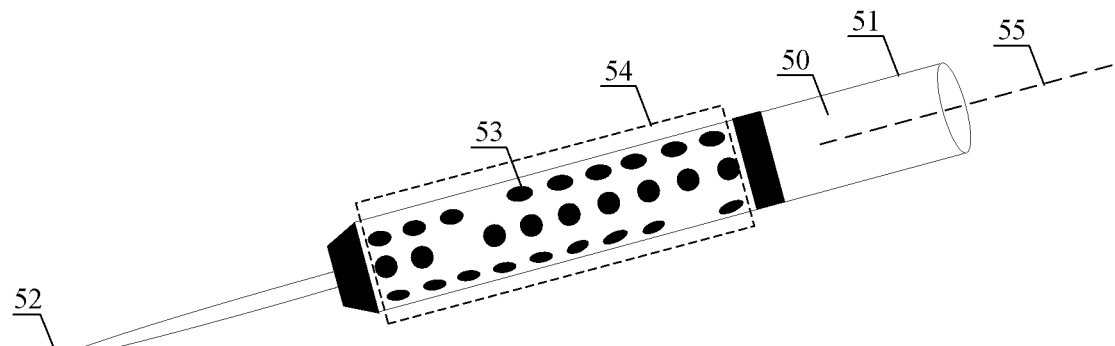
FIG. 5 is a schematic diagram of a navigation stick for spatial positioning according to an embodiment of this application.

FIG. 5 is a schematic diagram of a navigation stick for spatial positioning according to an embodiment of this application. The navigation stick 50 includes a stick body 51, a probe head 52, and a housing (not shown in the figure).

The probe head 52 is connected to an end of the stick body 51. In some embodiments, the probe head 52 is a needle-shaped probe head, and a needle tip position of the probe head is used as a to-be-detected position for spatial positioning to position any point in space, thereby improving the accuracy of spatial positioning. In some embodiments, a material of the probe head 52 is a metal material or ceramic material. In some embodiments, the stick body 51 is a cylinder or a prism. When the stick body 51 is a cylinder, an outer surface thereof is more convenient to distribute marker points and make the marker points have a good display effect at any angle, which improves the recognizability and recognition accuracy of the marker points.

The stick body 51 has an accommodation cavity (not shown in the figure) inside, and a circuit assembly (not shown in the figure) for driving the navigation stick 50 is placed in the accommodation cavity. In some embodiments, the inside of the stick body 51 is a hollow structure and has an accommodation cavity. The accommodation cavity is a cylindrical hollow space, which may be used to store a power supply and the circuit assembly. In some embodiments, the circuit assembly includes a circuit board. In some embodiments, the circuit board is a printed circuit board (PCB) or a flexible printed circuit (FPC) board. In some embodiments, the circuit assembly includes circuit components or semiconductor devices, such as processing chips, radio frequency antennas, resistors, or capacitors.

The housing is sleeved on the outside of the stick body 51, and an outer surface of the housing has a marker point array 54 for positioning the navigation stick 50. In some embodiments, the shape of the housing is determined by the stick body 51. For example, when the stick body 51 is cylindrical, the housing is a cylindrical housing for distributing the marker point array 54 and protecting the stick body 51.

In some embodiments, the housing is detachably connected to the stick body 51. In some embodiments, when conditions permit, the housing may be sleeved outside of another surgical instrument. In this case, a new navigation stick can be formed, which can effectively reduce the quantity of devices in the spatial positioning system, so that the application scenarios of the spatial positioning method provided in the embodiments of this application are more abundant, and the consumption of production materials can be reduced, having an environmental protection effect.

In some embodiments, the marker point array 54 includes n marker point columns distributed along an axial direction of the stick body 51, n being an integer greater than 1. The axial direction of the stick body 51 refers to a direction parallel to a central axis 55 of the stick body. In some embodiments, the quantity n of the marker point columns in the marker point array 54 is determined by a radius of the cylinder where the stick body 51 is located, which is used to ensure that at least two marker point columns are visible when the navigation stick 50 is observed at any angle. In some embodiments, when the navigation stick 50 is observed at any angle, there are three visible marker point columns, and one of the marker point columns is an alternate marker point column.

In some embodiments, distributions of marker points 53 in any two marker point columns are different. The positions of the marker point columns where the marker points 53 are located in the marker point array 54 may be determined through marker point distribution patterns of the marker points 53.

In some embodiments, each marker point column 54 includes a same quantity of marker points 53, and distributions of marker points 53 in any two marker point columns 54 are different. In some embodiments, the marker points 53 are active marker points or passive marker points. The active marker points refer to marker points that require power to realize a display function. The passive marker points do not need power to provide energy, and realize a marking function through marker point patterns or marker point materials. In some embodiments, different navigation sticks 50 have different quantities of marker points 53 in marker point columns 54, and different navigation sticks 50 in the image can be distinguished through the quantities of marker points in the marker point columns. The marker point column includes marker point positions and blank positions, the marker point positions have the marker points 53, and the blank positions do not have the marker points 53. Distributions of marker point positions and blank positions in any two marker point columns 54 are different.

Figure 6:
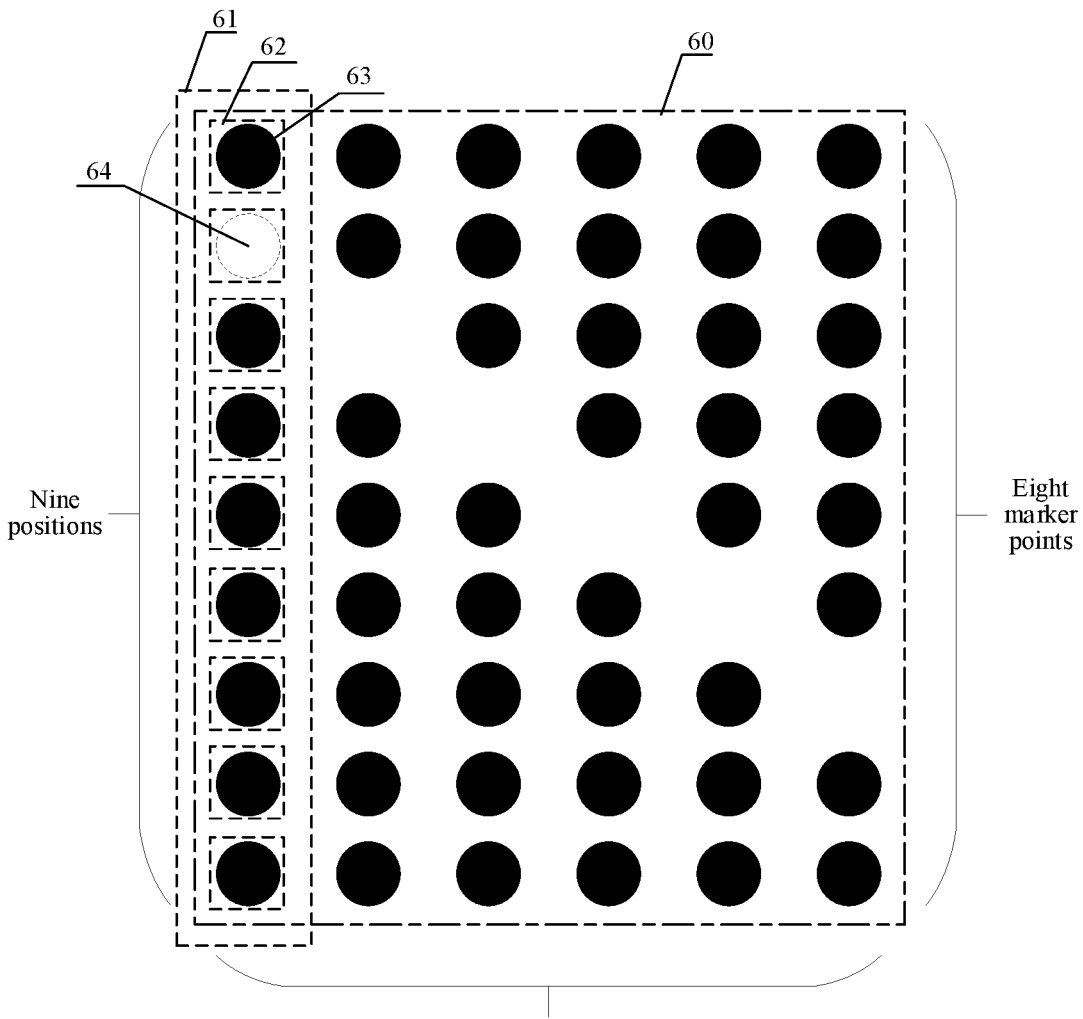
FIG. 6 is an exemplary schematic diagram of a marker point distribution pattern in a marker point array.

In an exemplary embodiment, FIG. 6 is a schematic diagram of a marker point distribution pattern in a marker point array. The marker point array 60 includes six marker point columns 61, and each marker point column 61 has nine positions 62. Among the nine positions of each marker point column, there are eight marker point positions with marker points 63 distributed and one is a blank position 64, and no marker point 63 is distributed on the blank position 64. A sorting position of the blank position 64 in the marker point column 61 can determine the position of the marker point column 61 in the marker point array 60. In FIG. 6, the blank position 64 of the first marker point column is the second position, the blank position 64 of the second marker point column is the third position, and so on. If it is known that the blank position 64 is in the sorting position, the position of the marker point column 61 where the blank position 64 is located in the marker point array 60 can be determined according to the foregoing relationship.

In some embodiments, a button (not shown in the figure) is disposed on the stick body 51 of the navigation stick 50 for the user to operate. In some embodiments, the button is a function switching button, and the function switching button is disposed on the other end of the stick body 51 to improve the usability of the spatial positioning system.

FIG. 7 is a flowchart of a spatial positioning method according to an embodiment of this application. The method may be applied to a computer device. For example, an execution entity of each step may be the terminal 10 of the spatial positioning system shown in FIG. 1. The method may include the following steps (701 to 705):

Step 701: Obtain an image obtained from a camera by photographing a target scene.

The camera is a device that uses the principle of optical imaging to form images and use negatives to record images, and is an optical device used for photography. In modern social life, there are many devices that can record images, which all have the characteristics of cameras, such as medical imaging devices or astronomical observation devices. An optical imaging system of the camera is designed according to the principle of geometric optics, and through the lens, a scene image is accurately focused on an image plane through the straight line propagation, refraction, or reflection of light. In some embodiments, the camera may be installed in the terminal. In some embodiments, the camera is a monocular camera. The type of the camera and the type of the computer device on which the camera is installed are not limited in this application.

The target scene refers to a scene presented in a specific space. In some embodiments, the target scene is a spatial scene of a real physical environment in neurosurgery.

The foregoing image is an objective reflection of the target scene, includes relevant information of objects in the target scene, and is an information source of the spatial positioning method provided in this implementation. In some embodiments, the image includes a navigation stick located in the target scene. The navigation stick is a surgical instrument for spatial positioning. In some embodiments, an outer surface of the navigation stick has a marker point array for locating the navigation stick. The marker point array is an array formed by marker points according to a specific feature distribution, and a corresponding marker point distribution pattern may be presented in the image, and may be recognized by the computer device. Position information of the navigation stick can be obtained through the marker point distribution pattern in the marker point array.

The camera photographs the target scene according to a camera model to obtain the image. The foregoing camera model refers to that the camera photographs a three-dimensional space where the target scene is located, and projects the three-dimensional space where the target scene is located into a two-dimensional plane image, to establish a mapping relationship between the three-dimensional space and the two-dimensional plane image.

In some embodiments, a coordinate system corresponding to the three-dimensional space includes a world coordinate system, a local coordinate system, and a camera coordinate system. The foregoing world coordinate system is an absolute coordinate system of the spatial positioning system. Before a user coordinate system is established, coordinates of all points in the image are determined by an origin of the coordinate system. The foregoing local coordinate system refers that a center of an object is used as a coordinate origin, and the rotation, translation, and other operations of the object are carried out around the local coordinate system. In this case, when the object model performs an operation such as rotation or translation, the local coordinate system also performs the corresponding rotation or translation. In some embodiments, the local coordinate system is a three-dimensional rectangular coordinate system established with a specific point in the navigation stick as a coordinate origin. The foregoing camera coordinate system is a three-dimensional rectangular coordinate system established with a focus center of the camera as an origin and an optical axis of the camera as a Z axis.

In some embodiments, the coordinate system corresponding to the two-dimensional plane image includes an image coordinate system and an imaging plane coordinate system. The image coordinate system refers a rectangular coordinate system u-v established in pixels with an upper left corner of an image as an origin. An abscissa u and an ordinate v of a pixel are a column number and a row number in an image array thereof respectively. Since the image coordinate system only represents a column number and a row number of a pixel in the digital image, and does not use a physical unit to represent a physical position of the pixel in the image, it is necessary to establish an imaging plane coordinate system x-y expressed in physical units (for example, centimeters). (x, y) represents coordinates of the imaging plane coordinate system measured in physical units. In the imaging plane coordinate system, the origin is defined at an intersection of the optical axis of the camera and the imaging plane, which is referred to as a principal point of the image and is generally located at the center of the image.

In some embodiments, the origin of the camera coordinate system is an optical center of the camera, the x-axis and y-axis in the imaging plane coordinate system are parallel to the X-axis and Y-axis in the camera coordinate system, and the z-axis is the optical axis of the camera, which is perpendicular to a graphics plane. The intersection of the optical axis of the camera and the imaging plane is the origin of the image coordinate system. The image coordinate system is a two-dimensional rectangular coordinate system.

Figure 8:
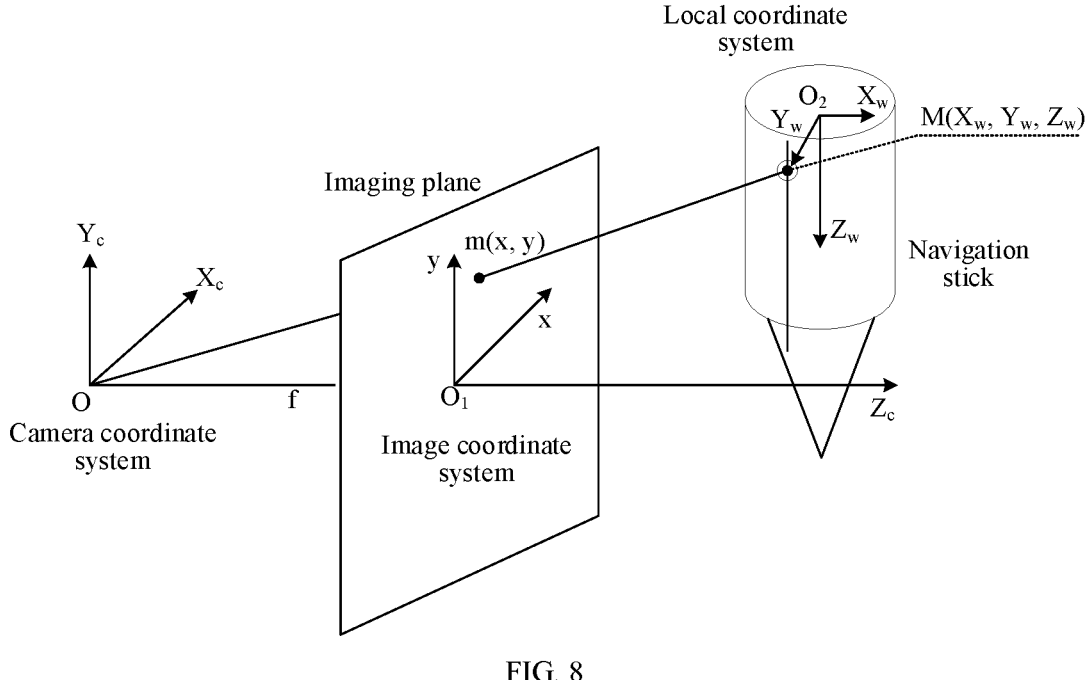
FIG. 8 is an exemplary schematic diagram of a camera imaging model.

FIG. 8 is a schematic diagram of a camera imaging model. A navigation stick is projected onto an imaging plane through an optical axis center point O1 of a camera, and a camera model (also referred to as a pinhole model) is established, including a local coordinate system corresponding to the navigation stick, an image coordinate system corresponding to the imaging plane, and a camera coordinate system corresponding to the camera. A coordinate origin O2 of the local coordinate system is a projection point of a first marker point in a first marker point column on the navigation stick on the axis of the cylinder, a coordinate origin of the camera coordinate system is point O, and a coordinate origin of the image coordinate system is the optical axis center point O1 of the camera, where a distance from O to O1 is a focal length f Coordinates of a marker point M on the navigation stick are expressed as (Xw, Yw, Zw) in the local coordinate system corresponding to the navigation stick, are expressed as (Xc, Yc, Zc) in the camera coordinate system corresponding to the camera, and are expressed as (x, y) in the image coordinate system corresponding to the imaging plane Step 702: Determine three-dimensional position coordinates of marker points included in the image in a three-dimensional coordinate system corresponding to the navigation stick according to marker point information in the image.

The marker point information includes position information of the marker points. In some embodiments, the marker point information further includes shape information of the marker points, and the shape information of the marker points refers to shape information of a pattern of the marker points. In some embodiments, the pattern of the marker points includes a combination of one or more shapes such as circle, square, and sector. The position information of the marker points refers to positions of the marker points in the image and positions of the marker points in a marker point array. In some embodiments, the marker point information is used for indicating the positions of the marker points included in the image in the marker point array. The three-dimensional position coordinates of the marker points included in the image in the three-dimensional coordinate system corresponding to the navigation stick can be determined according to the marker point information in the image.

Step 703: Determine position information of the camera in the three-dimensional coordinate system corresponding to the navigation stick according to two-dimensional position coordinates of the marker points in an image coordinate system corresponding to the image and the three-dimensional position coordinates of the marker points in the three-dimensional coordinate system corresponding to the navigation stick.

In some embodiments, the image coordinate system corresponding to the image is an image coordinate system or an imaging plane coordinate system included in the coordinate system corresponding to the two-dimensional plane image. In some embodiments, the three-dimensional coordinate system corresponding to the navigation stick is a local coordinate system established with a specific point in the navigation stick as a coordinate origin. A center of a circle surrounded by centers of first marker points of marker point columns in the marker point array is selected as the coordinate origin, and the coordinate origin is on the axis of the navigation stick.

In some embodiments, the two-dimensional position coordinates of the marker points in the image coordinate system corresponding to the image and the three-dimensional position coordinates of the marker points in the three-dimensional coordinate system corresponding to the navigation stick are position information of the marker points. The two-dimensional position coordinates of the marker points in the image coordinate system corresponding to the image are position information of the marker points in the image, and the three-dimensional position coordinates of the marker points in the three-dimensional coordinate system corresponding to the navigation stick are position information of the marker points in the marker point array.

In some embodiments, the position information of the camera in the three-dimensional coordinate system corresponding to the navigation stick includes coordinates of the camera in the foregoing local coordinate system.

Step 704: Determine a spatial transformation relationship between the three-dimensional coordinate system corresponding to the navigation stick and a three-dimensional coordinate system corresponding to the camera based on the position information of the camera in the three-dimensional coordinate system corresponding to the navigation stick.

The spatial transformation relationship refers to a one-to-one correspondence between the two coordinate systems. In some embodiments, the spatial transformation relationship between the three-dimensional coordinate system corresponding to the navigation stick and the three-dimensional coordinate system corresponding to the camera is a one-to-one correspondence between the foregoing local coordinate system and the foregoing camera coordinate system.

The spatial transformation relationship is the basis for coordinate transformation. The coordinate transformation is the description of a position of a spatial entity and the process of transforming from one coordinate system to another. For example, (a set of) coordinates of a point in one coordinate system are transformed to (another set of) coordinates in a new coordinate system according to the spatial transformation relationship. The new coordinate system may be a coordinate system of the same type as the original coordinate system, such as a new coordinate system obtained by translation or rotation of an original coordinate axis; or may be a different type of coordinate system, such as changing from a rectangular coordinate system to a polar coordinate system.

Step 705: Determine, based on three-dimensional position coordinates of a to-be-detected position of the navigation stick in the three-dimensional coordinate system corresponding to the navigation stick and the spatial transformation relationship, three-dimensional position coordinates of the to-be-detected position of the navigation stick in the three-dimensional coordinate system corresponding to the camera, and use the three-dimensional position coordinates of the to-be-detected position of the navigation stick in the three-dimensional coordinate system corresponding to the camera as spatial position information of the to-be-detected position of the navigation stick.

The to-be-detected position of the navigation stick refers to a detection point located on the navigation stick and used to indicate a position of a specific point in space. In some embodiments, the to-be-detected position of the navigation stick is a needle tip position or a stick tip position of the navigation stick.

In some embodiments, the three-dimensional position coordinates of the to-be-detected position of the navigation stick in the three-dimensional coordinate system corresponding to the navigation stick are coordinates of the needle tip of the navigation stick in the foregoing local coordinate system.

According to the spatial transformation relationship, coordinate transformation is performed on the three-dimensional position coordinates of the to-be-detected position of the navigation stick in the three-dimensional coordinate system corresponding to the navigation stick, to obtain the three-dimensional position coordinates of the to-be-detected position of the navigation stick in the three-dimensional coordinate system corresponding to the camera.

In some embodiments, the three-dimensional position coordinates of the to-be-detected position of the navigation stick in the three-dimensional coordinate system corresponding to the camera are coordinates of the needle tip of the navigation stick in the foregoing camera coordinate system.

To sum up, according to the technical solutions provided in the embodiments of this application, a photographing range of a camera is used as a spatial positioning range, and only a navigation stick and a terminal are used to form a spatial positioning system. A marker point distribution pattern and marker point information of marker points in an image photographed by the camera at any angle may be extracted. Three-dimensional position coordinates of the marker points included in the image in a three-dimensional coordinate system corresponding to the navigation stick are determined through the marker point information. Two-dimensional position coordinates of the marker points in an image coordinate system corresponding to the image and the three-dimensional position coordinates determined above are used as the basis to estimate a camera pose, to obtain a spatial transformation relationship between the three-dimensional coordinate system corresponding to the navigation stick and the image coordinate system corresponding to the image. A to-be-detected position where the navigation stick is located is spatially positioned according to the spatial transformation relationship, to obtain three-dimensional position coordinates of the to-be-detected position in the three-dimensional coordinate system corresponding to the camera. Therefore, the spatial transformation relationship between the three-dimensional coordinate system corresponding to the navigation stick and the three-dimensional coordinate system corresponding to the camera is determined, so that both the camera and the navigation stick can be moved arbitrarily, which improves the movement flexibility of the navigation stick, expands the spatial positioning range, improves the flexibility of spatial positioning, and reduces the costs of spatial positioning.

FIG. 9 is a flowchart of a spatial positioning method according to another embodiment of this application. The method may be applied to the application running environment shown in FIG. 1. The method may include the following steps (901 to 910):

Step 901: Obtain an image obtained from a camera by photographing a target scene.

Step 902: Recognize centers of the marker points included in the image.

Image preprocessing is performed on the image. In some embodiments, the image preprocessing includes grayscale processing, binarization processing, filtering processing, and denoising processing.

Shape information such as circularity, convexity, area, shape size, and inertia ratio are used to remove non-marker points and marker points that deviate from a projection direction in the target scene. The non-marker points in the target scene may be removed through the shape size, circularity, and convexity. For example, a circularity of a regular hexagon is higher than that of a square, and a circularity of a circle is higher than that of a regular hexagon. The marker points that deviate from the projection direction can be removed through the inertia ratio of the shape. The elongation of the shape may be measured by the inertia ratio. For example, for a circle, the inertia ratio is 1; for an ellipse, the inertia ratio is between 0 and 1; and for a line, the inertia ratio is 0.

In some embodiments, the centers of the marker points included in the image are recognized through blob analysis. The purpose of the Blob analysis is to detect and analyze the marker points in the image, to obtain information such as positions, shapes, and directions of the marker points, and a topological relationship (that is, an inclusion relationship) between the marker points. The marker points may be recognized based on such information.

The Blob analysis mainly includes the following image processing technologies:

1. Image segmentation: Blob analysis is a type of feature analysis of closed shapes. The image is segmented into an object and a background before blob analysis. Image segmentation is a large category of image processing technologies. The segmentation technologies to be provided in Blob analysis include: direct input, fixed hard threshold, relative hard threshold, dynamic hard threshold, fixed soft threshold, relative soft threshold, pixel mapping, and threshold image. The fixed soft threshold and relative soft threshold methods can eliminate the spatial quantization error to a specific extent, thereby improving the calculation accuracy of a target feature component.

2. Morphological operation: The purpose of morphological operation is to remove the impact of noise points.

3. Connectivity analysis: It is to convert a target from a pixel level to the connected component level.

4. Eigenvalue calculation: For each target, feature components are calculated, including features such as area, perimeter, and centroid coordinates.

5. Scene description: It is to describe a topological relationship between objects in a scene.

Step 903: Detect a target straight line passing through the centers of the marker points.

The target straight line is a straight line that passes through a quantity of the centers of the marker points that meets a condition. The quantity of the centers of the marker points that the target straight line passes through meeting the condition means that the quantity of the centers of the marker points that the target straight line passes through meeting a threshold. In some embodiments, the threshold is determined by the marker points in the marker point column. In some embodiments, the threshold is the quantity of the marker points in the marker point column. In some embodiments, the threshold is determined by the quantity of marker points in the marker point column and a reasonable error.

In some embodiments, the target straight line passing through the centers of the marker points is detected through Hough Transform. Hough Transform is a type of feature detection widely used in image analysis, computer vision, and digital image processing. Hough Transform is used for recognizing features in objects, such as straight lines. Hough transform is to obtain lines corresponding to marker points in a parameter plane by calculating marker points in an image plane, and then calculate a target straight line in the image plane from an intersection of the lines corresponding to the marker points in the parameter plane. The target straight line corresponds to a marker point column in a marker point array.

Step 904: Obtain a marker point distribution pattern of a marker point column corresponding to the target straight line.

The marker point column corresponding to the target straight line refers to a column of marker points formed by the marker points that the target straight line passes through. In the image, a quantity of marker points in each marker point column is fixed. The quantity of the centers of the marker points passed through are detected to determine a straight line with a quantity meeting the condition as the target straight line. It can be determined that the marker points that the target straight line passes through are located in the same column in the marker point array. Therefore, the target straight line corresponds to a marker point column in the image. The centers of the marker points in the marker point column are on the target straight line.

The marker point distribution pattern refers to the marker point column to which the marker points belong in the marker point array and a sorting position of the marker points in the marker point column.

In an exemplary embodiment, step 904 may be implemented through the following steps.

Step 1: Determine a first marker point in the marker point column corresponding to the target straight line.

The first marker point refers to a marker point located at a highest or lowest position in the image in the marker point column corresponding to the target straight line.

In an example, the first marker point in the marker point column, that is, the first of the marker points in the marker point column, is determined according to a vertical axis coordinate in the imaging plane coordinate system, that is, a y-axis coordinate. A neurosurgery scene is used as an example. An incision of a surgical entry of a patient is upward, so that a needle tip of the navigation stick is downward when entering the incision for spatial positioning. Therefore, during camera imaging, a Y value of a first marker point on each marker point column in the imaging plane coordinate system is the largest, so that the first marker point in the marker point column can be determined.

Step 2: Obtain first distances between the remaining marker points and the first marker point.

The remaining marker points refer to other marker points except the first marker point in the marker point column corresponding to the target straight line.

The first distances are calculated based on two-dimensional position coordinates of the marker points in the marker point column in the image coordinate system corresponding to the image. The first distances refer to distances between the remaining marker points and the first marker point in the image coordinate system. According to the first distance, a position sorting of the remaining marker points in the marker point column is determined. For example, a marker point with the smallest first distance among the remaining marker points is the closest to the first marker point, and the marker point is then a second marker point, and so on. Finally, the position sorting of the marker points in the marker point column is obtained, which includes a sorting position of any marker point in the corresponding marker point column.

Step 3: Obtain second distances between adjacent marker points in the marker point column corresponding to the target straight line.

The second distances are calculated based on two-dimensional position coordinates of the marker points in the marker point column in the image coordinate system corresponding to the image. The second distances refer to distances between the adjacent marker points in the image coordinate system.

A blank position in the marker point column is determined according to the second distances. For example, in a possible implementation of the marker point array, a blank position of a first marker point column is at the second position in the marker point column. In this case, the first marker point is at the first position in the marker point column, the second marker point is located at the third position of the marker point column, and a second distance between the first marker point and the second marker point is greater than the second distances between other adjacent marker points. Therefore, according to the case that the second distance between the first marker point and the second marker point is greater than the second distances between other adjacent marker points, it can be determined that the marker point column is the first marker point column in the marker point array shown in FIG. 6.

Step 905: Determine marker point information of the marker point column corresponding to the target straight line according to the marker point distribution pattern.

In some embodiments, the marker point information includes a position of the marker point column corresponding to the target straight line in the marker point array and positions of the marker points that the target straight line passes through in the marker point array.

Step 906: Determine three-dimensional position coordinates of marker points included in the image in a three-dimensional coordinate system corresponding to the navigation stick based on marker point information.

In a possible implementation, a coordinate origin of the three-dimensional coordinate system corresponding to the navigation stick is located on a central axis of a cylinder where the navigation stick is located, where a z-axis is downward along the direction of the axis, a y-axis points to a center of the first marker point of the first marker point column in the marker point array, and an x-axis may be determined by the right-hand criterion. In this case, based on a position of a marker point column to which a marker point belongs in the marker point array, coordinates of the marker point in the x-axis and y-axis directions in the three-dimensional coordinate system corresponding to the navigation stick can be determined. Since the foregoing first distances and second distances are fixed in the marker point array, coordinates of a marker point in the z-axis direction in the three-dimensional coordinate system corresponding to the navigation stick can be determined based on a sorting position of the marker point in the marker point column. That is, the three-dimensional position coordinates of the marker points included in the image in the three-dimensional coordinate system corresponding to the navigation stick are determined based on the marker point information.

Step 907: Determine the position information of the camera in the three-dimensional coordinate system corresponding to the navigation stick by performing pose estimation processing on the camera according to the two-dimensional position coordinates of the marker points in the image coordinate system corresponding to the image and the three-dimensional position coordinates of the marker points in the three-dimensional coordinate system corresponding to the navigation stick.

The pose estimation processing refers to determining an orientation and a direction of a three-dimensional target object. In the embodiments of this application, the pose estimation processing is performed on the camera to determine the position information of the camera in the three-dimensional coordinate system corresponding to the navigation stick.

In some embodiments, the pose estimation processing is performed on the camera by using a method of using Perspective n-Point (PnP) to resolve a PnP problem. The method of using PnP to resolve a PnP problem means that corresponding parameters of the camera, object point coordinates, and corresponding pixel values are known, and the position and the pose of the camera are estimated according to 3D-2D matching. In the embodiments of this application, the camera parameters can be determined by the selected camera, the object points are the marker points, the coordinates of the object points are the position information of the marker points in the three-dimensional coordinate system corresponding to the navigation stick, and the pixel values corresponding to the object points are the position information of the marker points in the two-dimensional coordinate system corresponding to the image. The position information of the camera in the three-dimensional coordinate system corresponding to the navigation stick is determined by matching the position information of the marker points in the three-dimensional coordinate system corresponding to the navigation stick and the position information of the marker points in the two-dimensional coordinate system corresponding to the image. In some embodiments, the position information of the camera in the three-dimensional coordinate system corresponding to the navigation stick includes six degrees of freedom, of which three degrees of freedom represent the position of the camera, and the other three degrees of freedom represent the angle of the camera.

Step 908: Obtain position information of the camera in the three-dimensional coordinate system corresponding to the camera.

Parameter information of the camera is obtained. In some embodiments, the parameter information of the camera includes focus center information of the camera, which is used for determining the position information of the camera in the camera coordinate system, that is, the position information of the camera in the three-dimensional coordinate system corresponding to the camera.

Step 909: Determine a transformation matrix between the three-dimensional coordinate system corresponding to the navigation stick and the three-dimensional coordinate system corresponding to the camera based on the position information of the camera in the three-dimensional coordinate system corresponding to the navigation stick and the position information of the camera in the three-dimensional coordinate system corresponding to the camera.

In an example, the coordinates of the camera in the local coordinate system determined by the navigation stick and the coordinates of the camera in the camera coordinate system are known, and a spatial transformation relationship between the local coordinate system and the camera coordinate system may then be resolved. The spatial transformation relationship is used for performing coordinate transformation between the local coordinate system and the camera coordinate system for a same point in space. In some embodiments, the spatial transformation relationship includes the transformation matrix.

Step 910: Determine, based on three-dimensional position coordinates of a to-be-detected position of the navigation stick in the three-dimensional coordinate system corresponding to the navigation stick and the spatial transformation relationship, three-dimensional position coordinates of the to-be-detected position of the navigation stick in the three-dimensional coordinate system corresponding to the camera as spatial position information of the to-be-detected position of the navigation stick.

To sum up, according to the technical solutions provided in the embodiments of this application, the position information of the marker points in the marker point array is obtained by accurately recognizing the centers of the marker points and calculating the first distances and the second distances between the centers of the marker points, and the marker points are then mapped from the two-dimensional plane to the three-dimensional space, which establishes a good foundation for obtaining the spatial transformation relationship between the coordinate systems in the camera model.

In addition, according to the technical solutions provided in the embodiments of this application, the PnP algorithm is used to estimate the pose of the camera based on the two-dimensional coordinates and the three-dimensional coordinates of the marker points, to accurately obtain the position information of the camera in the local coordinate system, so that the spatial transformation relationship can be more accurate, and accurate spatial positioning information can be obtained.

In an exemplary embodiment, the image includes a first image and a second image, and the first image and the second image are images obtained by photographing the target scene by the camera at different moments. After step 910 is performed, the following steps are further performed:

Step 911: Determine a movement distance of the navigation stick based on spatial position information of the to-be-detected position of the navigation stick in the first image and spatial position information of the to-be-detected position of the navigation stick in the second image.

The moment corresponding to the first image is the first moment, and the moment corresponding to the second image is the second moment.

In some embodiments, a distance between coordinates of the needle tip of the navigation stick in the first image and coordinates of the needle tip of the navigation stick in the second image is calculated, and a linear distance of the position change caused by the movement of the needle tip of the navigation stick from the first moment to the second moment is determined.

In an exemplary embodiment, the image includes at least two image frames. After step 910 is performed, the following steps are further performed:

Step 912: Determine a connection line between the to-be-detected positions of the navigation stick in adjacent image frames based on spatial position information of the to-be-detected positions of the navigation stick in the image frames.

The image frames are the smallest units that form a video. The connection line between the to-be-detected positions of the navigation stick in adjacent image frames shows a position change of the to-be-detected positions of the navigation stick between the adjacent image frames, that is, a trajectory of the to-be-detected positions of the navigation stick between the adjacent image frames.

Step 913: Obtain a trajectory formed by the to-be-detected positions of the navigation stick in the at least two image frames based on the connection line between the to-be-detected positions of the navigation stick in the adjacent image frames.

The lines between the to-be-detected positions of the navigation stick in the adjacent image frames from a start image frame to an end image frame are connected end-to-end to obtain the trajectory formed by the movement of the to-be-detected position of the navigation stick between the start image frame and the end image frame.

In some embodiments, the execution order of steps 914 and 915, and steps 912 and 913 is not specifically limited. In an exemplary embodiment, after step 913 is performed, the following steps are further performed:

Step 914: Determine a length of the connection line between the to-be-detected positions of the navigation stick in the adjacent image frames based on the spatial position information of the to-be-detected positions of the navigation stick in the image frames.

The length of the connection line between the to-be-detected positions of the navigation stick in the adjacent image frames is a length of the trajectory formed by the to-be-detected positions of the navigation stick between the adjacent image frames.

Step 915: Obtain a length of the trajectory formed by the to-be-detected positions of the navigation stick in the at least two image frames based on the length of the connection line between the to-be-detected positions of the navigation stick in the adjacent image frames.

Lengths of the connection lines between the to-be-detected positions of the navigation stick in the adjacent image frames from the start image frame to the end image frame are accumulated to obtain the length of the trajectory formed by the movement of the to-be-detected position of the navigation stick between the start image frame and the end image frame.

To sum up, according to the technical solutions provided in the embodiments of this application, based on the method of performing spatial positioning on the to-be-detected position, the to-be-detected position is extended to achieve the functions of spatial ranging and spatial contour line drawing, which enriches the applications of the spatial positioning method and satisfies the diversified requirements of users.

The following is an apparatus embodiment of this application, which can be used to execute the method embodiments of this application. For details not disclosed in the apparatus embodiment of this application, reference may be made to the method embodiments of this application.

Figure 10:
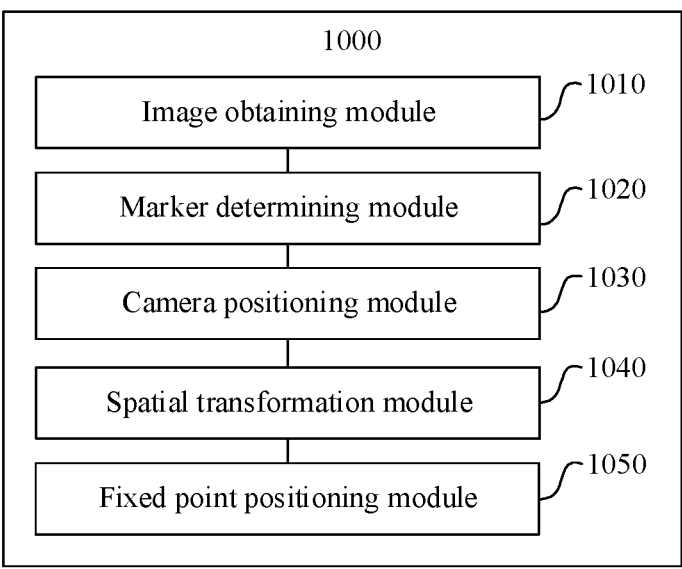
FIG. 10 is a block diagram of a spatial positioning apparatus according to an embodiment of this application.

FIG. 10 is a block diagram of a spatial positioning apparatus according to an embodiment of this application. The apparatus has functions of implementing the foregoing spatial positioning method. The functions may be implemented by hardware, or may be implemented by hardware executing corresponding software. The apparatus may be a terminal or may be disposed in a terminal. The apparatus 1000 may include: an image obtaining module 1010, a marker determining module 1020, a camera positioning module 1030, a spatial transformation module 1040 and a fixed point positioning module 1050.

The image obtaining module 1010 is configured to obtain an image from a camera by photographing a target scene, the image including a navigation stick located in the target scene, and an outer surface of the navigation stick having a marker point array for locating the navigation stick.

The marker determining module 1020 is configured to determine three-dimensional position coordinates of marker points included in the image in a three-dimensional coordinate system corresponding to the navigation stick according to marker point information in the image, the marker point information being used for indicating positions of the marker points included in the image in the marker point array.

The camera positioning module 1030 is configured to determine position information of the camera in the three-dimensional coordinate system corresponding to the navigation stick according to two-dimensional position coordinates of the marker points in an image coordinate system corresponding to the image and the three-dimensional position coordinates of the marker points in the three-dimensional coordinate system corresponding to the navigation stick.

The spatial transformation module 1040 is configured to determine a spatial transformation relationship between the three-dimensional coordinate system corresponding to the navigation stick and a three-dimensional coordinate system corresponding to the camera based on the position information of the camera in the three-dimensional coordinate system corresponding to the navigation stick.

The fixed point positioning module 1050 is configured to determine, based on three-dimensional position coordinates of a to-be-detected position of the navigation stick in the three-dimensional coordinate system corresponding to the navigation stick and the spatial transformation relationship, three-dimensional position coordinates of the to-be-detected position of the navigation stick in the three-dimensional coordinate system corresponding to the camera as spatial position information of the to-be-detected position of the navigation stick.

Figure 11:
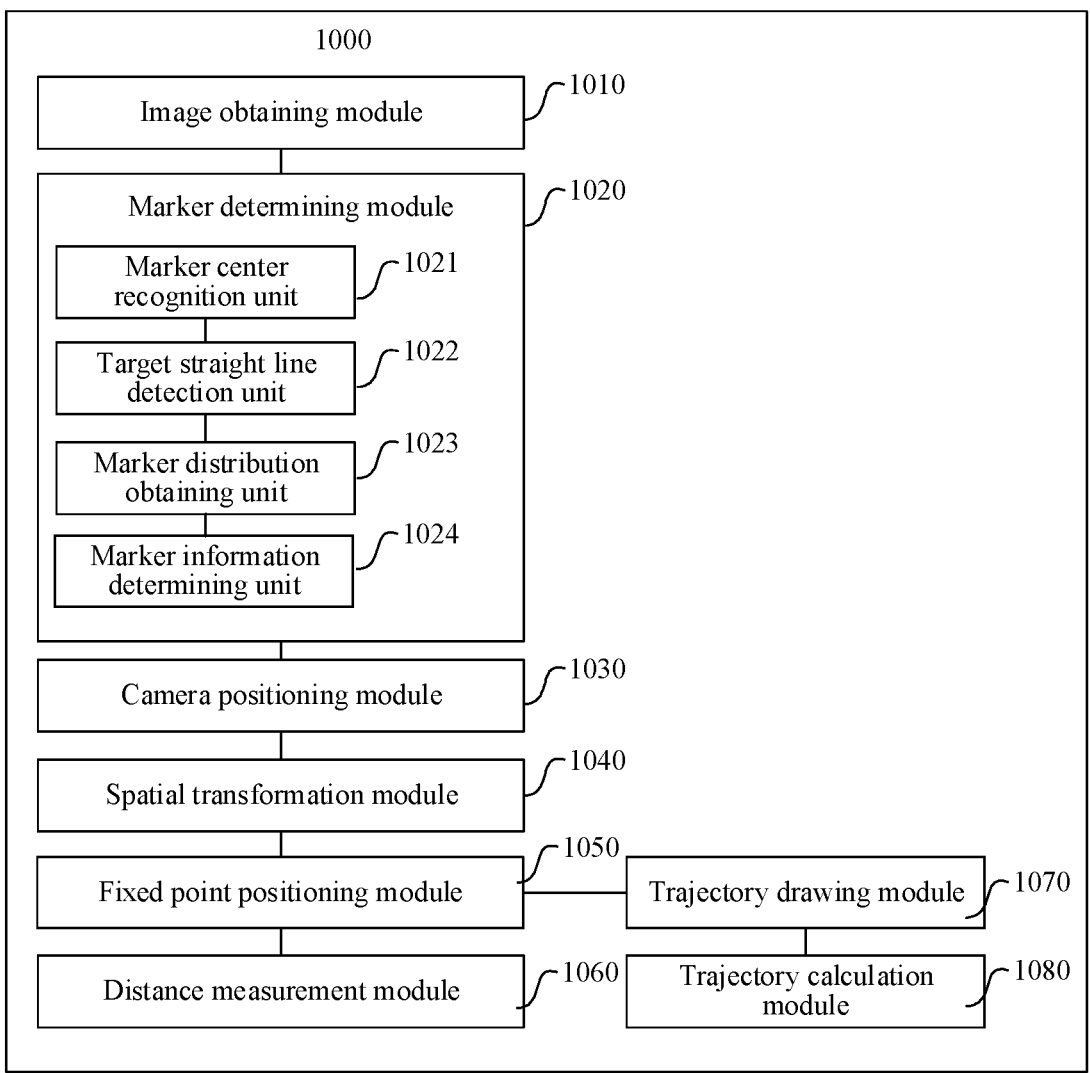
FIG. 11 is a block diagram of a spatial positioning apparatus according to another embodiment of this application.

In an exemplary embodiment, referring to FIG. 11, the marker determining module 1020 includes:

a marker center recognition unit 1021, configured to recognize centers of the marker points included in the image;

a target straight line detection unit 1022, configured to detect a target straight line passing through the centers of the marker points, a quantity of the centers of the marker points that the target straight line passes through meets a condition;

a marker distribution obtaining unit 1023, configured to obtain a marker point distribution pattern of a marker point column corresponding to the target straight line, the marker point column corresponding to the target straight line referring to a column of marker points formed by the marker points that the target straight line passes through; and a marker information determining unit 1024, configured to determine marker point information of the marker point column corresponding to the target straight line according to the marker point distribution pattern, the marker point information including a position of the marker point column corresponding to the target straight line in the marker point array and positions of the marker points that the target straight line passes through in the marker point array.

In an exemplary embodiment, referring to FIG. 11, the marker distribution obtaining unit 1023 is configured to:

determine a first marker point in the marker point column corresponding to the target straight line, the first marker point referring to a marker point located at a highest or lowest position in the image in the marker point column corresponding to the target straight line;

obtain first distances between the remaining marker points and the first marker point, the remaining marker points referring to other marker points except the first marker point in the marker point column corresponding to the target straight line, and the first distances referring to distances between the remaining marker points and the first marker point in the image coordinate system; and obtain second distances between adjacent marker points in the marker point column corresponding to the target straight line, the second distances referring to distances between the adjacent marker points in the image coordinate system.

In an exemplary embodiment, referring to FIG. 10, the camera positioning module 1030 is configured to:

determine the position information of the camera in the three-dimensional coordinate system corresponding to the navigation stick by performing pose estimation processing on the camera according to the two-dimensional position coordinates of the marker points in the image coordinate system corresponding to the image and the three-dimensional position coordinates of the marker points in the three-dimensional coordinate system corresponding to the navigation stick.

In an exemplary embodiment, referring to FIG. 10, the spatial transformation module 1040 is configured to:

obtain position information of the camera in the three-dimensional coordinate system corresponding to the camera; and determine a transformation matrix between the three-dimensional coordinate system corresponding to the navigation stick and the three-dimensional coordinate system corresponding to the camera based on the position information of the camera in the three-dimensional coordinate system corresponding to the navigation stick and the position information of the camera in the three-dimensional coordinate system corresponding to the camera, the spatial transformation relationship including the transformation matrix.

In an exemplary embodiment, referring to FIG. 11, the image includes a first image and a second image, and the first image and the second image are images obtained by photographing the target scene by the camera at different moments. The apparatus 1000 further includes:

a distance measurement module 1060, configured to determine a movement distance of the navigation stick based on spatial position information of the to-be-detected position of the navigation stick in the first image and spatial position information of the to-be-detected position of the navigation stick in the second image.

In an exemplary embodiment, referring to FIG. 11, the image includes at least two image frames; and the apparatus 1000 further includes:

a trajectory drawing module 1070, configured to determine a connection line between the to-be-detected positions of the navigation stick in adjacent image frames based on spatial position information of the to-be-detected positions of the navigation stick in the image frames; and obtain a trajectory formed by the to-be-detected positions of the navigation stick in the at least two image frames based on the connection line between the to-be-detected positions of the navigation stick in the adjacent image frames.

In an exemplary embodiment, referring to FIG. 11, the apparatus 1000 further includes:

a trajectory calculation module 1080, configured to determine a length of the connection line between the to-be-detected positions of the navigation stick in the adjacent image frames based on the spatial position information of the to-be-detected positions of the navigation stick in the image frames; and obtain a length of the trajectory formed by the to-be-detected positions of the navigation stick in the at least two image frames based on the length of the connection line between the to-be-detected positions of the navigation stick in the adjacent image frames.

To sum up, according to the technical solutions provided in the embodiments of this application, a photographing range of a camera is used as a spatial positioning range, and only a navigation stick and a terminal device are used to form a spatial positioning system. A marker point distribution pattern of marker points in an image photographed by the camera at any angle may be extracted. Two-dimensional coordinates and three-dimensional coordinates of the marker points are determined and used as the basis to estimate a camera pose, to obtain a spatial transformation relationship between a local coordinate system and a camera coordinate system. A to-be-detected position is spatially positioned according to the spatial transformation relationship, which expands the spatial positioning range, improves the flexibility of spatial positioning, and reduces the costs of spatial positioning.

Figure 12:
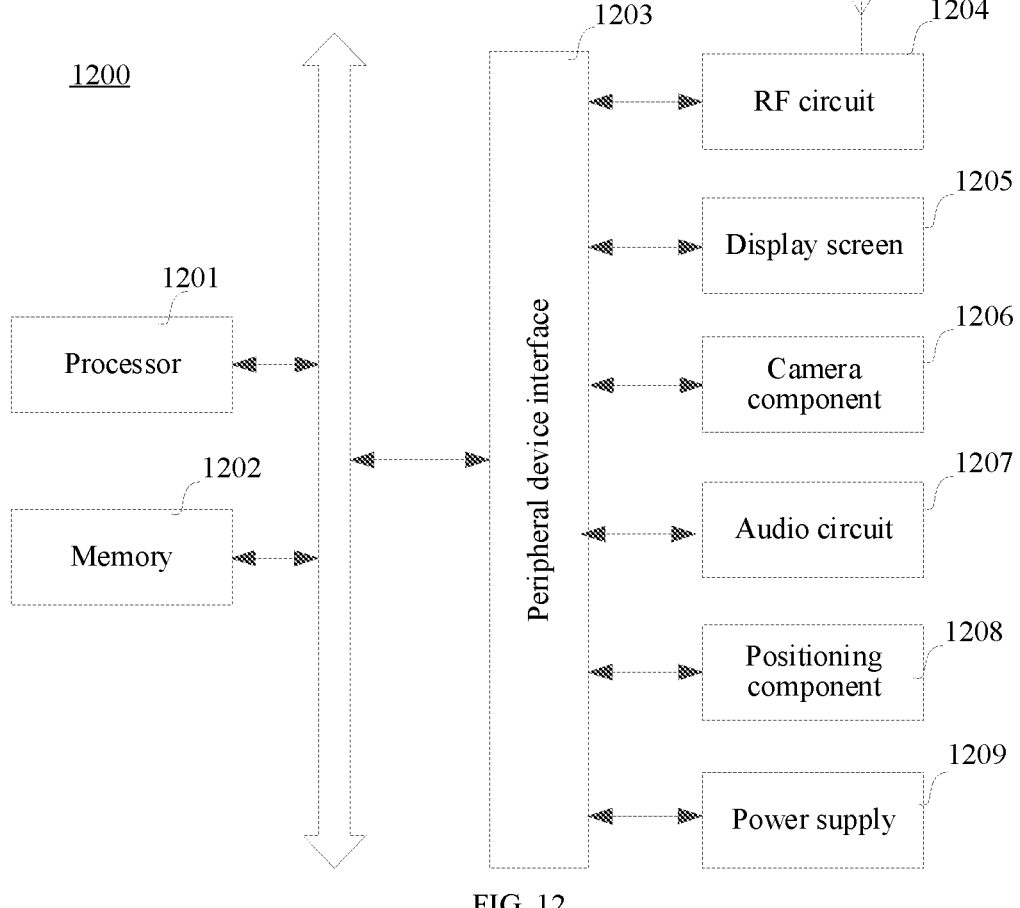
FIG. 12 is a structural block diagram of a computer device according to an embodiment of this application.

FIG. 12 is a structural block diagram of a terminal 1200 according to an embodiment of this application. The terminal 1200 may be an electronic device such as a mobile phone, a tablet computer, a game console, an ebook reader, a multimedia player, a wearable device, or a PC. The terminal is configured to implement the spatial positioning method provided in the foregoing embodiments. The terminal may be the terminal 10 in the spatial positioning system shown in FIG. 1. Specifically:

Generally, the terminal 1200 includes a processor 1201 and a memory 1202.

The processor 1201 may include one or more processing cores, for example, a 4-core processor or an 8-core processor. The processor 1201 may be implemented by using at least one hardware form of a digital signal processor (DSP), a field programmable gate array (FPGA), and a programmable logic array (PLA). The processor 1201 may alternatively include a main processor and a coprocessor. The main processor is configured to process data in an awake state, also referred to as a central processing unit (CPU). The coprocessor is a low-power processor configured to process data in a standby state. In some embodiments, the processor 1201 may be integrated with a graphics processing unit (GPU). The GPU is configured to render and draw content that needs to be displayed on a display. In some embodiments, the processor 1201 may further include an AI processor. The AI processor is configured to process computing operations related to ML.

The memory 1202 may include one or more computer-readable storage media that may be non-transitory. The memory 1202 may further include a high-speed random access memory and a non-volatile memory, such as one or more magnetic disk storage devices or flash storage devices. In some embodiments, the non-transient computer-readable storage medium in the memory 1202 is configured to store at least one instruction, at least one program, a code set, or an instruction set, the at least one instruction, the at least one program, the code set, or the instruction set being configured to be executed by one or more processors to implement the foregoing spatial positioning method.

In some embodiments, the terminal 1200 may In some embodiments include a peripheral interface 1203 and at least one peripheral. The processor 1201, the memory 1202, and the peripheral interface 1203 may be connected by using a bus or a signal cable. Each peripheral may be connected to the peripheral interface 1203 by using a bus, a signal cable, or a circuit board. Specifically, the peripheral includes: at least one of a radio frequency (RF) circuit 1204, a display screen 1205, a camera assembly 1206, an audio circuit 1207, a positioning component 1208, and a power supply 1209.

A person skilled in the art may understand that the structure shown in FIG. 12 does not constitute a limitation to the terminal 1200, and the terminal may include more or fewer components than those shown in the figure, or some components may be combined, or a different component deployment may be used.

In an exemplary embodiment, a computer-readable storage medium is further provided, the storage medium storing at least one instruction, at least one program, a code set, or an instruction set, the at least one instruction, the at least one program, the code set, or the instruction set, when executed by the processor, implementing the foregoing spatial positioning method.

In some embodiments, the computer-readable storage medium may include: a read-only memory (ROM), a RAM, a solid state drive (SSD), an optical disc, or the like. The RAM may include a resistance random access memory (ReRAM) and a dynamic random access memory (DRAM).

In an exemplary embodiment, a computer program product or a computer program is further provided. The computer program product or the computer program includes computer instructions, and the computer instructions are stored in a computer-readable storage medium. A processor of a computer device reads the computer instructions from the computer-readable storage medium, and executes the computer instructions, to cause the computer device to perform the foregoing spatial positioning method.

It is to be understood that "plurality of" mentioned in the specification means two or more. And/or describes an association relationship for describing associated objects and represents that three relationships may exist. For example, A and/or B may represent the following three cases: Only A exists, both A and B exist, and only B exists. The character "I" generally indicates an "or" relationship between the associated objects. In addition, the step numbers described in this specification merely schematically show a possible execution sequence of the steps. In some other embodiments, the steps may not be performed according to the number sequence. For example, two steps with different numbers may be performed simultaneously, or two steps with different numbers may be performed according to a sequence contrary to the sequence shown in the figure. This is not limited in the embodiments of this application.

In this application, the term "unit" or "module" in refers to a computer program or part of the computer program that has a predefined function and works together with other related parts to achieve a predefined goal and may be all or partially implemented by using software, hardware (e.g., processing circuitry and/or memory configured to perform the predefined functions), or a combination thereof. Each unit or module can be implemented using one or more processors (or processors and memory). Likewise, a processor (or processors and memory) can be used to implement one or more modules or units. Moreover, each module or unit can be part of an overall module that includes the functionalities of the module or unit.

The foregoing descriptions are merely exemplary embodiments of this application, but are not intended to limit this application. Any modification, equivalent replacement, or improvement made within the spirit and principle of this application shall fall within the protection scope of this application.

What is claimed is:

1. A method for spatial positioning, performed by an electronic device, the method comprising:

obtaining an image from a camera by photographing a target scene, the image comprising a navigation stick located in the target scene, the navigation stick having a stick body, and an outer surface of the navigation stick having a marker point array for locating the navigation stick, wherein the marker point array comprises n marker point columns distributed along an axial direction of the stick body, n being an integer greater than 1, and each of the n marker point columns comprises a same quantity of marker points, and distributions of marker points in any two of the n marker point columns are different;

determining three-dimensional position coordinates of the marker points of the marker point array in the image in a three-dimensional coordinate system corresponding to the navigation stick according to marker point information in the image, the marker point information being used for indicating positions of the marker points in the image in the marker point array;

determining position information of the camera in the three-dimensional coordinate system corresponding to the navigation stick according to two-dimensional position coordinates of the marker points in an image coordinate system corresponding to the image and the three-dimensional position coordinates of the marker points in the three-dimensional coordinate system corresponding to the navigation stick;

determining a spatial transformation relationship between the three-dimensional coordinate system corresponding to the navigation stick and a three-dimensional coordinate system corresponding to the camera based on the position information of the camera in the three-dimensional coordinate system corresponding to the navigation stick;

determining, based on three-dimensional position coordinates of a to-be-detected position of the navigation stick in the three-dimensional coordinate system corresponding to the navigation stick and the spatial transformation relationship, three-dimensional position coordinates of the to-be-detected position of the navigation stick in the three-dimensional coordinate system corresponding to the camera; and using the three-dimensional position coordinates of the to-be-detected position of the navigation stick in the three-dimensional coordinate system corresponding to the camera as spatial position information of the to-be-detected position of the navigation stick.

2. The method according to claim 1, further comprising:

recognizing centers of the marker points in the image;

detecting a target straight line passing through the centers of the marker points, a number of the centers of the marker points that the target straight line passes through satisfying a condition;

obtaining a marker point distribution pattern of a marker point column corresponding to the target straight line, the marker point column corresponding to the target straight line referring to a column of marker points formed by the marker points that the target straight line passes through; and determining marker point information of the marker point column corresponding to the target straight line according to the marker point distribution pattern, the marker point information comprising a position of the marker point column corresponding to the target straight line in the marker point array and positions of the marker points that the target straight line passes through in the marker point array.

3. The method according to claim 2, wherein the obtaining the marker point distribution pattern of the marker point column corresponding to the target straight line comprises:

determining a first marker point in the marker point column corresponding to the target straight line, the first marker point referring to a marker point located at a highest or lowest position in the image in the marker point column corresponding to the target straight line;

obtaining first distances between the remaining marker points and the first marker point, the remaining marker points referring to other marker points except the first marker point in the marker point column corresponding to the target straight line, and the first distances referring to distances between the remaining marker points and the first marker point in the image coordinate system; and obtaining second distances between adjacent marker points in the marker point column corresponding to the target straight line, the second distances referring to distances between the adjacent marker points in the image coordinate system.

4. The method according to claim 1, wherein the determining position information of the camera in the three-dimensional coordinate system corresponding to the navigation stick according to two-dimensional position coordinates of the marker points in the image coordinate system corresponding to the image and the three-dimensional position coordinates of the marker points in the three-dimensional coordinate system corresponding to the navigation stick comprises:

determining the position information of the camera in the three-dimensional coordinate system corresponding to the navigation stick by performing pose estimation processing on the camera according to the two-dimensional position coordinates of the marker points in the image coordinate system corresponding to the image and the three-dimensional position coordinates of the marker points in the three-dimensional coordinate system corresponding to the navigation stick.

5. The method according to claim 1, wherein the determining the spatial transformation relationship between the three-dimensional coordinate system corresponding to the navigation stick and the three-dimensional coordinate system corresponding to the camera based on the position information of the camera in the three-dimensional coordinate system corresponding to the navigation stick comprises:

obtaining position information of the camera in the three-dimensional coordinate system corresponding to the camera; and determining a transformation matrix between the three-dimensional coordinate system corresponding to the navigation stick and the three-dimensional coordinate system corresponding to the camera based on the position information of the camera in the three-dimensional coordinate system corresponding to the navigation stick and the position information of the camera in the three-dimensional coordinate system corresponding to the camera, wherein the spatial transformation relationship includes the transformation matrix.

6. The method according to claim 1, wherein the obtaining the image from the camera by photographing the target scene comprises: obtaining a first image and a second image from the camera by photographing the target scene at different moments; and the method further comprises:

determining a movement distance of the navigation stick based on spatial position information of the to-be-detected position of the navigation stick in the first image and spatial position information of the to-be-detected position of the navigation stick in the second image.

7. The method according to claims 1, wherein the image comprises at least two image frames; and the method further comprises:

determining a connection line between the to-be-detected positions of the navigation stick in adjacent image frames based on spatial position information of the to-be-detected positions of the navigation stick in the image frames; and obtaining a trajectory formed by the to-be-detected positions of the navigation stick in the at least two image frames based on the connection line between the to-be-detected positions of the navigation stick in the adjacent image frames.

8. The method according to claim 7, further comprising:

determining a length of the connection line between the to-be-detected positions of the navigation stick in the adjacent image frames based on the spatial position information of the to-be-detected positions of the navigation stick in the image frames; and obtaining a length of the trajectory formed by the to-be-detected positions of the navigation stick in the at least two image frames based on the length of the connection line between the to-be-detected positions of the navigation stick in the adjacent image frames.

9. The method according to claim 1, wherein the camera is a monocular camera.

10. The method according to claim 1, wherein the navigation stick further comprises a probe head and a housing, wherein the probe head is connected to an end of the stick body and a position of the probe head is configured to indicate the to-be-detected position of the stick for spatial positioning.

11. The method according to claim 10, wherein the stick body has an accommodation cavity inside, and a circuit assembly for driving the navigation stick is placed in the accommodation cavity; and the housing is sleeved on outside of the stick body, and an outer surface of the housing has the marker point array for locating the navigation stick.

12. The method according to claim 1, wherein each marker point column comprises marker point positions and blank positions, the marker point positions have the marker points, and the blank positions do not have the marker points; and distributions of marker point positions and blank positions in any two marker point columns are different.

13. The method according to claim 10, wherein the housing is detachably connected to the stick body.

14. A computer device, comprising a processor and a memory, the memory storing at least one instruction, at least one program, a code set, or an instruction set, the at least one instruction, the at least one program, the code set, or the instruction set being loaded and executed by the processor to implement a method for spatial positioning, the method comprising:

obtaining an image from a camera by photographing a target scene, the image comprising a navigation stick located in the target scene, the navigation stick having a stick body, and an outer surface of the navigation stick having a marker point array for locating the navigation stick, wherein the marker point array comprises n marker point columns distributed along an axial direction of the stick body, n being an integer greater than 1, and each of the n marker point columns comprises a same quantity of marker points, and distributions of marker points in any two of the n marker point columns are different;

determining three-dimensional position coordinates of the marker points of the marker point array in the image in a three-dimensional coordinate system corresponding to the navigation stick according to marker point information in the image, the marker point information being used for indicating positions of the marker points in the image in the marker point array;

determining position information of the camera in the three-dimensional coordinate system corresponding to the navigation stick according to two-dimensional position coordinates of the marker points in an image coordinate system corresponding to the image and the three-dimensional position coordinates of the marker points in the three-dimensional coordinate system corresponding to the navigation stick;

determining a spatial transformation relationship between the three-dimensional coordinate system corresponding to the navigation stick and a three-dimensional coordinate system corresponding to the camera based on the position information of the camera in the three-dimensional coordinate system corresponding to the navigation stick;

determining, based on three-dimensional position coordinates of a to-be-detected position of the navigation stick in the three-dimensional coordinate system corresponding to the navigation stick and the spatial transformation relationship, three-dimensional position coordinates of the to-be-detected position of the navigation stick in the three-dimensional coordinate system corresponding to the camera; and using the three-dimensional position coordinates of the to-be-detected position of the navigation stick in the three-dimensional coordinate system corresponding to the camera as spatial position information of the to-be-detected position of the navigation stick.

15. The computer device according to claim 14, wherein the method for spatial positioning further comprises:

recognizing centers of the marker points in the image;

detecting a target straight line passing through the centers of the marker points, a number of the centers of the marker points that the target straight line passes through satisfying a condition;

obtaining a marker point distribution pattern of a marker point column corresponding to the target straight line, the marker point column corresponding to the target straight line referring to a column of marker points formed by the marker points that the target straight line passes through; and determining marker point information of the marker point column corresponding to the target straight line according to the marker point distribution pattern, the marker point information comprising a position of the marker point column corresponding to the target straight line in the marker point array and positions of the marker points that the target straight line passes through in the marker point array.

16. The computer device according to claim 15, wherein the obtaining the marker point distribution pattern of the marker point column corresponding to the target straight line comprises:

determining a first marker point in the marker point column corresponding to the target straight line, the first marker point referring to a marker point located at a highest or lowest position in the image in the marker point column corresponding to the target straight line;

obtaining first distances between the remaining marker points and the first marker point, the remaining marker points referring to other marker points except the first marker point in the marker point column corresponding to the target straight line, and the first distances referring to distances between the remaining marker points and the first marker point in the image coordinate system; and obtaining second distances between adjacent marker points in the marker point column corresponding to the target straight line, the second distances referring to distances between the adjacent marker points in the image coordinate system.

17. The computer device according to claim 14, wherein the determining position information of the camera in the three-dimensional coordinate system corresponding to the navigation stick according to two-dimensional position coordinates of the marker points in the image coordinate system corresponding to the image and the three-dimensional position coordinates of the marker points in the three-dimensional coordinate system corresponding to the navigation stick comprises:

determining the position information of the camera in the three-dimensional coordinate system corresponding to the navigation stick by performing pose estimation processing on the camera according to the two-dimensional position coordinates of the marker points in the image coordinate system corresponding to the image and the three- dimensional position coordinates of the marker points in the three-dimensional coordinate system corresponding to the navigation stick.

18. The computer device according to claim 14, wherein the determining the spatial transformation relationship between the three-dimensional coordinate system corresponding to the navigation stick and the three-dimensional coordinate system corresponding to the camera based on the position information of the camera in the three-dimensional coordinate system corresponding to the navigation stick comprises:

obtaining position information of the camera in the three-dimensional coordinate system corresponding to the camera; and determining a transformation matrix between the three-dimensional coordinate system corresponding to the navigation stick and the three-dimensional coordinate system corresponding to the camera based on the position information of the camera in the three-dimensional coordinate system corresponding to the navigation stick and the position information of the camera in the three-dimensional coordinate system corresponding to the camera, wherein the spatial transformation relationship includes the transformation matrix.

19. A non-transitory computer-readable storage medium, storing at least one instruction, at least one program, a code set, or an instruction set, and the at least one instruction, the at least one program, the code set, or the instruction set being loaded and executed by a processor to implement a method for spatial positioning, the method comprising:

obtaining an image from a camera by photographing a target scene, the image comprising a navigation stick located in the target scene, the navigation stick having a stick body, and an outer surface of the navigation stick having a marker point array for locating the navigation stick, wherein the marker point array comprises n marker point columns distributed along an axial direction of the stick body, n being an integer greater than 1, and each of the n marker point columns comprises a same quantity of marker points, and distributions of marker points in any two of the n marker point columns are different;

determining three-dimensional position coordinates of the marker points of the marker point array in the image in a three-dimensional coordinate system corresponding to the navigation stick according to marker point information in the image, the marker point information being used for indicating positions of the marker points in the image in the marker point array;

determining position information of the camera in the three-dimensional coordinate system corresponding to the navigation stick according to two-dimensional position coordinates of the marker points in an image coordinate system corresponding to the image and the three-dimensional position coordinates of the marker points in the three-dimensional coordinate system corresponding to the navigation stick;

determining a spatial transformation relationship between the three-dimensional coordinate system corresponding to the navigation stick and a three-dimensional coordinate system corresponding to the camera based on the position information of the camera in the three-dimensional coordinate system corresponding to the navigation stick;

determining, based on three-dimensional position coordinates of a to-be-detected position of the navigation stick in the three-dimensional coordinate system corresponding to the navigation stick and the spatial transformation relationship, three-dimensional position coordinates of the to-be-detected position of the navigation stick in the three-dimensional coordinate system corresponding to the camera; and using the three-dimensional position coordinates of the to-be-detected position of the navigation stick in the three-dimensional coordinate system corresponding to the camera as spatial position information of the to-be-detected position of the navigation stick.

* * * * *